United States Patent
Hoiseth et al.

(10) Patent No.: US 7,608,278 B2
(45) Date of Patent: Oct. 27, 2009

(54) FORMULATIONS OF HYDROPHOBIC PROTEINS IN AN IMMUNOGENIC COMPOSITION HAVING IMPROVED TOLERABILITY

(75) Inventors: Susan Kay Hoiseth, Montebello, NY (US); Thomas Newell Metcalf, III, Wind Gap, PA (US); Yury Vladimirovich Matsuka, New Windsor, NY (US); Michael Hagen, Pittsford, NY (US); Lakshmi Khandke, Nanuet, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/585,050

(22) PCT Filed: Dec. 28, 2004

(86) PCT No.: PCT/US2004/043792

§ 371 (c)(1),
(2), (4) Date: Jun. 29, 2006

(87) PCT Pub. No.: WO2005/065708

PCT Pub. Date: Jul. 21, 2005

(65) Prior Publication Data

US 2007/0122433 A1    May 31, 2007

Related U.S. Application Data

(60) Provisional application No. 60/533,122, filed on Dec. 30, 2003.

(51) Int. Cl.
*A61K 45/00* (2006.01)
*A61K 47/00* (2006.01)
*A61K 49/00* (2006.01)

(52) U.S. Cl. .................. 424/278.1; 424/9.1; 424/9.2

(58) Field of Classification Search .................. 424/9.1, 424/9.2, 278.1; 435/278.1
See application file for complete search history.

(56) References Cited

U.S. PATENT DOCUMENTS 5,084,561 A * 1/1992 Bredt et al. .................. 530/417
2002/0136741 A1 9/2002 Zlotnick

FOREIGN PATENT DOCUMENTS

WO    WO 00/45841    8/2000

OTHER PUBLICATIONS

Buchanan, Susan K.; Current Opinion in Structural Biology 9:455-461 (1999).
Celozzi, E.; et al., Journal of Pharmacological Methods 4:205-209 (1980).
Comereski, C.R.; et al., Fundamental and Applied Toxicology 6:335-338 (1986).
Idanpaan-Heikkila, I.; et al., Vaccine 14(9):886-891 (1996).
Matsuka, Yury V.; et al., Journal of Protein Chemistry 17(7):719-728 (1998).
Waite, Douglas C.; et al, Vaccine 19:3957-3967 (2001).
Jeurissen SH M et al; Infection and Immunity, 55(1):253-257 (1987).

* cited by examiner

*Primary Examiner*—Rodney P. Swartz
(74) *Attorney, Agent, or Firm*—J. Darrell Fontenot; Kelly M. Sullivan

(57) ABSTRACT

The present invention provides a method for producing a less-painful immunogenic composition of a hydrophobic protein in a pharmaceutically acceptable carrier suitable for administering to a mammal, comprising the steps of (a) solubilizing said hydrophobic protein with a zwitterionic detergent to make a first composition; (b) altering said first composition, such that the altered composition produces a reduction in pain as measured in the rat footpad model as compared to said first composition.

38 Claims, 1 Drawing Sheet

FORMULATIONS OF HYDROPHOBIC PROTEINS IN AN IMMUNOGENIC COMPOSITION HAVING IMPROVED TOLERABILITY

This application is the US national phase of international application PCT/US2004/043792 filed on Dec. 28, 2004, which designated the US and claims priority to U.S. Provisional Application No. 60/533,122, filed Dec. 30, 2003. The entire contents of these applications are incorporated herein by reference.

FIELD OF THE INVENTION

This invention relates to non-painful or less-painful immunogenic and pharmaceutical compositions used to induce an immune response to hydrophobic membrane proteins, such as porins. These compositions are used for prevention or treatment of mammalian diseases, such as meningitis or gonorrhea.

BACKGROUND OF THE INVENTION

Most protein-based pharmaceuticals contain either no detergent, or relatively mild detergents, such as TWEEN® 80 (polysorbate 80) or TWEEN® 20. However, these mild detergents often are not able to solubilize certain hydrophobic membrane proteins. When hydrophobic membrane proteins are separated from membranes, their exposed hydrophobic regions interact, causing the protein molecules to aggregate and precipitate from aqueous solutions. Such proteins can be solubilized by detergents which have affinity both for hydrophobic groups and for water. Ionic detergents bind to the exposed hydrophobic regions of membrane proteins as well as to the hydrophobic core of water-soluble proteins. Because of their charge, these detergents often denature the protein by disrupting ionic and hydrogen bonds. At high concentrations, for example, sodium dodecylsulfate completely denatures proteins. In contrast, at high concentrations nonionic detergents solubilize biological membranes by forming mixed micelles of detergent, phospholipid, and hydrophobic membrane proteins. However, denatured proteins and proteins in mixed micelles are generally not optimal for use as immunogenic compositions. At low concentrations, these detergents may not solubilize hydrophobic membrane proteins. Zwitterionic detergents have been shown to efficiently solubilize hydrophobic membrane proteins extracted from native membranes and promote refolding of such proteins when produced recombinantly. See Matsuka, Y. V. et al., J. Protein Chemistry 17(7):719-728 (1998). As discussed below, there is a present need for effective immunogenic compositions comprising membrane proteins, for example from the pathogens, N. meningitidis and N. gonorrhoeae.

N. meningitidis

Neisseria meningitidis, a Gram-negative encapsulated diplococcus, is an obligate human pathogen and the causative agent of meningococcal meningitis, one of the most devastating forms of meningitis. These bacteria are found worldwide and can cause sporadic and epidemic disease. Person-to-person transfer of N. meningitidis occurs mainly via the airborne route, and is particularly a problem in places where people are in close quarters, such as prisons, military camps, dormitories, school classrooms, and daycare centers. At any one time, between 2 and 10% of individuals in the population carry this organism asymptomatically (Greenfield, et al., J. Infec. Dis. 1971, 123:67-73; Moore, et al., Scientific American 1994, 38-45; Romero, et al., Clinical Microbiology Review 1994, 7:559-575). With such a high carrier rate, the threat or potential for outbreaks or epidemics is always present.

Designated by serogroup, serological classification of N. meningitidis is based on the capsular polysaccharide composition of the particular strain. Among the meningococci there are at least thirteen different serogroups: A, B, C, 29-E, H, I, X, L, W135, X, Y and Z. Of these serogroups, A, B, C and W135 are the most frequent cause of disease. The nature of the capsule in serogroups A, C and W135 has led to the development of useful immunogenic compositions against these serogroups. However, the serogroup B capsular polysaccharide is thought to be unsuitable for use in humans. Because of the need for immunogenic compositions against serogroup B, efforts have concentrated on characterization of the antigenicity and immunogenicity of various membrane proteins, such as porins. Some of the major protein antigens include the outer membrane proteins (OMP) such as class 1 (Por A, a cation specific porin), class 2 or 3 (Por B, an anion specific protein), and to a lesser extent class 4, class 5 OMPs (Rmp, and Opc and Opa opacity associated proteins) and lipidated surface proteins.

N. gonorrhoeae

Gonorrhea is at the present time one of the most widespread venereal diseases worldwide, with several hundred cases occurring in the United States alone each year. The causative agent of the disease is the gonococcus Neisseria gonorrhoeae, a bacterium which has throughout its history developed resistance both to traditional antibiotic treatment, and, to some extent, to the bactericidal activity of normal human serum. The inability to control the infection by traditional means has given rise to the need for an immunogenic composition that can effectively prevent the infection.

The greatest concentration of study in the area of developing an immunogenic composition for gonorrhea has been focused on the outer membrane proteins. A number of immunogenic compositions employing portions of the gonococcal membrane have been described, for example, in U.S. Pat. Nos. 4,203,971; 4,288,557; and 4,681,761. Most of these compositions, however, contain a mixture of protein and extraneous cellular materials, the presence of which frequently elicit adverse inflammatory or physiological responses along with the desired immune response. Therefore, a need exists for immunogenic compositions with purer forms of bacterial antigens.

One candidate for an immunogenic composition for gonorrhea is the specific outer membrane protein known as Protein I, or Por. Por is a hydrophobic membrane protein and is the major outer membrane protein of N. gonorrhoeae, functioning as a porin. Porins are believed to operate in the cell by channeling low molecular weight substances across the hydrophobic lipid outer membrane. There are a number of features of Por that make it an interesting candidate for use in an immunogenic composition. First, it is at least partly responsible for serotype specificity in Neisseria. Second, it appears to be surface exposed in its native state and induces the production of opsonins, which are antibodies which bind to the surface of an infectious organism, facilitating the engulfment of the organism by phagocytes.

Two different major types of Por molecules have been demonstrated in gonococci, PorA (also known as PIA) and PorB (also known as PIB) based on peptide mapping and susceptibility to proteolysis. See Barrera et al., Infect.

Immun. 1984, 44:565-568; Blake et al., Infect. Immun. 1981, 33:212-222. This division has been found to correlate with serogroup patterns and pathogenesis. Gonococci expressing PorA are more likely to be associated with systemic infections, while those with PorB are generally associated with localized infection. See Buchanan et al., Infect. Immun. 1981, 32:985-994; Hildebrandt et al., Infect. Immun. 1978, 20:267-273. Substantially purified nucleic acid molecules encoding PIA are described in U.S. Pat. No. 5,736,361. Substantially purified nucleic acid molecules encoding PIB are described in U.S. Pat. No. 6,068,992.

Because of the potential beneficial immunogenic effect of hydrophobic membrane proteins, especially Por proteins, there remains an unfulfilled need for efficacious, tolerable subunit immunogenic compositions and methods of making them. More specifically there is a need for immunogenic compositions, consisting of meningococcal or gonnococcal hydrophobic membrane proteins, which are readily producible, safe, non-painful or less-painful and effective for treating and/or preventing infection.

SUMMARY OF THE INVENTION

One embodiment of the invention provides a non-painful composition of a hydrophobic protein suitable for injection in a human comprising: (a) a hydrophobic protein; (b) an amount of a zwitterionic detergent that is less than the amount required to solubilize the protein; and (c) an amount of a pharmaceutically acceptable nonionic detergent effective to maintain solubility of the protein in a pharmaceutically acceptable carrier. Embodiments of the invention also provide a method of immunizing a human, which method comprises parenterally administering the composition wherein the infectious agent is a human pathogen.

In another embodiment of the invention, a method for producing a less-painful immunogenic composition of a hydrophobic protein in a pharmaceutically acceptable carrier suitable for administering to a mammal is provided. The method comprises the steps of (a) solubilizing said hydrophobic protein with a zwitterionic detergent to make a first composition; (b) altering said first composition, such that the altered composition produces a reduction in pain as compared to said first composition. In other embodiments of the invention, methods for altering compositions comprising a hydrophobic protein with a zwitterionic detergent are provided which include (i) diluting the zwitterionic detergent, (ii) exchanging the zwitterionic detergent with a non-pain causing nonionic detergent, and (iii) adding a non-pain causing nonionic detergent but keeping the concentration of the zwitterionic detergent constant. In another embodiment, the altering step is diluting said zwitterionic detergent and wherein the hydrophobic protein is in a precipitated form.

In still another embodiment of the invention, a method of reducing the pain associated with administering an immunogenic composition comprising a hydrophobic protein and a zwitterionic detergent into a mammal is provided. The method comprises altering said composition, such that the altered composition is less painful as compared to the unaltered composition, and administering said immunogenic composition. In other embodiments of the invention, methods for altering compositions comprising a hydrophobic protein with a zwitterionic detergent are provides which include (i) diluting the zwitterionic detergent, (ii) exchanging the zwitterionic detergent with a non-pain causing nonionic detergent, and (iii) adding a non-pain causing nonionic detergent but keeping the concentration of the zwitterionic detergent constant. In another embodiment, the altering step is diluting said zwitterionic detergent and wherein the hydrophobic protein is in a precipitated form.

In a specific embodiment, the zwitterionic detergent is n-Tetradecyl-N,N-dimethyl-3-ammonio-1-propanesulfonate in a final concentration that is below its CMC and the nonionic detergent is alpha-[4-(1,1,3,3-tetramethylbutyl)phenyl]-omega-hydroxypoly(oxy-1,2-ethanediyl) in a final concentration that is above its critical micelle concentration (CMC).

In another embodiment of the invention, the solubility of the hydrophobic protein is maintained in said nonionic detergent. In an alternate embodiment of the invention, the altering step is diluting said zwitterionic detergent and wherein the hydrophobic protein is in a precipitated form.

In certain embodiments of the invention, pain is measured in the rat footpad model. In other embodiments, the altered composition produces at least about a 50% reduction in pain as measured in the rat footpad model as compared to the unaltered composition.

In still another embodiment of the invention, a method of reducing the pain associated with administering an immunogenic composition comprising a hydrophobic protein and a zwitterionic detergent into a mammal is provided. The method comprises altering said composition, such that the altered composition produces a reduction in pain as measured in the rat footpad model as compared to the unaltered composition, and administering said immunogenic composition, wherein the altered composition produces at least a 50% reduction in pain as measured in the rat footpad model as compared to the unaltered composition.

Other embodiments of the invention provide a method of maintaining solubility of a hydrophobic protein in an immunogenic composition, which method comprises: solubilizing a hydrophobic protein in a non-pain causing nonionic detergent, wherein non-pain causing nonionic detergent is alpha-[4-(1,1,3,3-tetramethylbutyl)phenyl]-omega-hydroxypoly(oxy-1,2-ethanediyl).

A particular embodiment of the invention provides a method for immunizing humans with compositions containing hydrophobic membrane proteins without causing pain, which method comprises selecting Triton X-100 as a pharmaceutically acceptable detergent for maintaining solubility of hydrophobic proteins in the final formulation; wherein the concentration of Triton X-100 is above the CMC.

In certain embodiments of the invention, the zwitterionic detergent is selected from the group consisting of n-Octyl-N,N-dimethyl-3-ammonio-1-propanesulfonate; n-Decyl-N,N-dimethyl-3-ammonio-1-propanesulfonate; n-Dodecyl-N,N-dimethyl-3-ammonio-1-propanesulfonate; n-Tetradecyl-N,N-dimethyl-3-ammonio-1-propanesulfonate; 3-(N,N-n-Hexadecyl-N,N-dimethyl-3-ammonio-1-propanesulfonate; 3-[(3-Cholamidopropyl)dimethylammonio]-1-propane-sulfonate; 3-[(3-Cholamidopropyl)dimethylammonio]-2-hydroxy-1-propanesulfonate; and n-Dodecyl-N,N-dimethylglycine. In a particular embodiment of the invention the zwitterionic detergent is n-Tetradecyl-N,N-dimethyl-3-ammonio-1-propanesulfonate.

In still other embodiments of the invention, the nonionic detergent is selected from the group consisting of alpha-[4-(1,1,3,3-tetramethylbutyl)phenyl]-omega-hydroxypoly(oxy-1,2-ethanediyl), Polyoxyethylene (20) sorbitan monolaurate, Polyoxyethylene (20) sorbitan monooleate and Polyoxyethylene (35) Lauryl Ether. In a particular embodiment of the invention the nonionic detergent is alpha-[4-(1,1,3,3-tetramethylbutyl)phenyl]-omega-hydroxypoly(oxy-1,2-ethanediyl).

In a certain embodiment of the invention, the zwitterionic detergent is n-Tetradecyl-N,N-dimethyl-3-ammonio-1-propanesulfonate in a final concentration that is below its CMC and the nonionic detergent is alpha-[4-(1,1,3,3-tetramethylbutyl)phenyl]-omega-hydroxypoly(oxy-1,2-ethanediyl) in a final concentration that is above its CMC.

In particular embodiments of the invention, the hydrophobic protein is an integral membrane protein. In other embodiments of the invention, the integral membrane protein is derived from an infectious agent selected from the group consisting of a bacterium, a virus, a parasite and a prion. In one embodiment the infectious agent is a bacterium and the integral membrane protein is a porin. In a specific embodiment, the integral membrane protein is a gonococcal porin or a Meningococcal porin.

In one embodiment of the invention, the detergent component of a pain causing composition is altered by either dilution of the detergent, exchange of the detergent, or addition of a non-pain causing detergent to produce an altered but non pain causing composition. In a particular embodiment of the invention, the altered composition produces at least a 50% reduction in pain as measured in the rat footpad model as compared to the unaltered composition. In a specific embodiment of the invention, the altered composition produces at least about a 75% reduction in pain as measured in the rat footpad model as compared to the altered composition. In another embodiment of the invention, the diluted or exchanged composition produces at least about a 90% reduction in pain as measured in the rat footpad model as compared to the unaltered composition.

DETAILED DESCRIPTION

Figure 1:
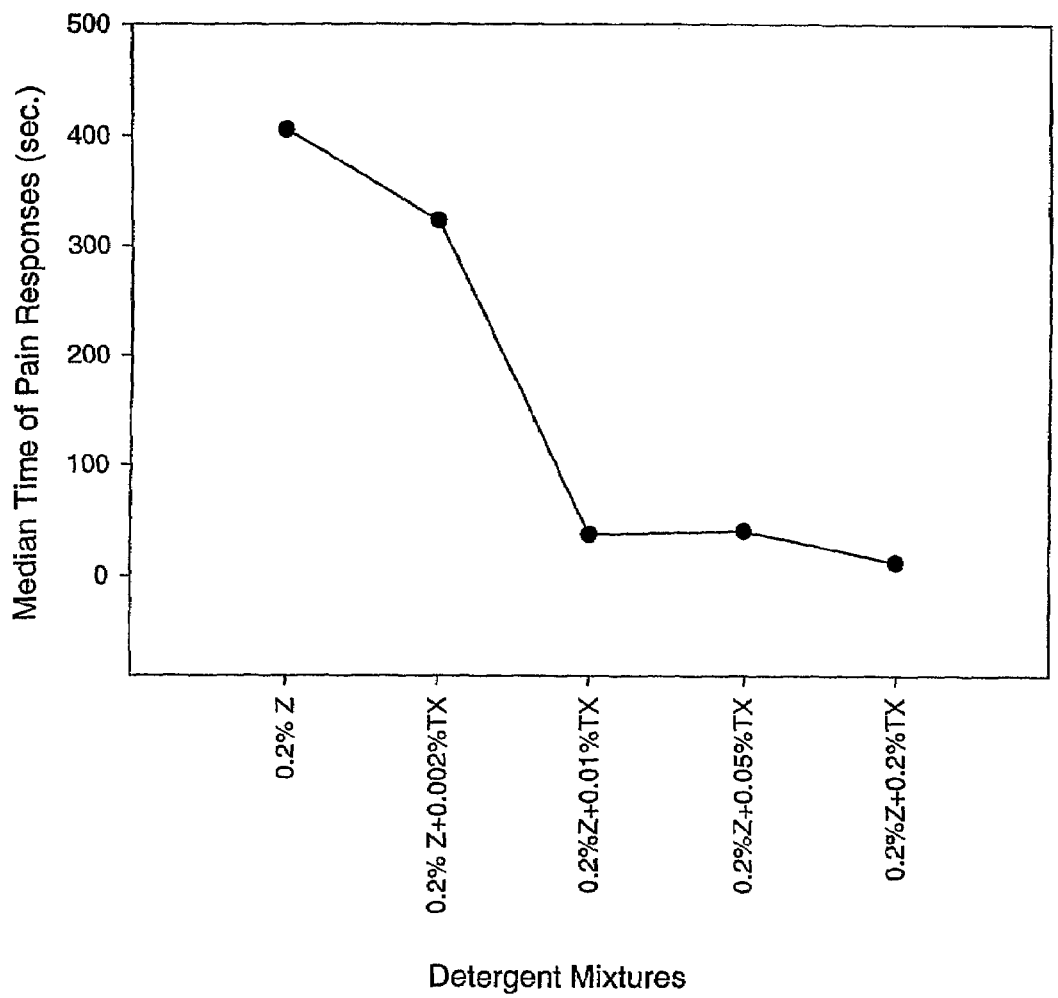
FIG. 1 This figure is a graphic representation of the pain associated with various immunogenic compositions of a painful zwitterionic detergent (Zwittergent® 3-12) and a non-painful nonionic detergent (Triton® X-100) after injection into the footpads of rats. The concentration of the painful zwitterionic detergent is held constant and increasing amounts of a second non-painful nonionic detergent is added.

Embodiments of the present invention provide for compositions of a hydrophobic protein, such as an hydrophobic membrane protein, particularly immunogenic compositions having acceptable tolerability. Embodiments of the present invention also provide for methods of producing the compositions.

While methods for producing immunogenic compositions in which the antigen is a hydrophobic protein have been previously disclosed, such compositions either contain detergents used for purification, which have now been found to cause pain in mammals upon injection, or mild detergents, such as TWEEN® 80 (polysorbate 80) or TWEEN® 20, which are not capable of solubilizing certain hydrophobic proteins. For example, hydrophobic proteins that are difficult to solubilize, such as integral membrane proteins, have been isolated and purified from cell membranes using zwitterionic detergents. However, one of the discoveries of the invention is that the presence of zwitterionic detergents in these immunogenic compositions causes pain to humans and rats upon injection and dramatically reduces the tolerability of resulting immunogenic composition to unacceptable levels.

Embodiments of the present invention relate to the unexpected discovery that immunogenic compositions comprising hydrophobic proteins administered in solutions comprising non-ionic detergents or in zwitterionic detergents below the critical micelle concentration have good tolerability to subjects. In another embodiment of the invention, the less painful or nonpain causing detergent is added to a level that is above its critical micelle concentration while the concentration of the pain causing detergent is kept constant and the resulting composition has improved tolerability when administered to subjects. As used herein, an immunogenic composition having "improved tolerability" refers to an immunogenic composition comprising a hydrophobic membrane protein and a detergent, which produces substantially less pain when injected into a subject as compared to the immunogenic composition where the hydrophobic protein is administered in 0.05% Zwittergent 3-14 as the only detergent component.

A human clinical study tested a recombinant gonococcal PorB ("rPorB") as a protective immunogenic composition candidate. The immunogenic composition contained 50 μg of recombinant gonococcal porin ("GC rPorB") in a volume of 0.5 ml of 10 mM phosphate buffered saline (PBS) and 0.03% (w/v) Zwittergent® ("Zw") 3-14, a zwitterionic detergent to solubilize the porin. However, injection of this composition showed poor tolerability by inducing an unacceptable level of pain at the site of injection. Each of the eight recipients receiving GC rPorB experienced immediate pain on injection (three severe, five moderate) regardless of adjuvant, which were two with each of the following adjuvants: 3-O-deacylated monophosphoryl lipid A (MPL) (Corixa, Hamilton, Mont.), aluminum phosphate, MPL plus aluminum phosphate, or no adjuvant. This pain resolved within 20 minutes following the injection.

Embodiments of the present invention resulted, in part, from an effort to elucidate the source of pain in a recombinant subunit immunogenic composition. Pain on injection is a serious clinical issue affecting the tolerability of parenteral immunogenic compositions. Because the pain described above occurred in all GC rPorB immunogenic composition groups, regardless of adjuvant, it was unlikely to be due to a particular adjuvant or an interaction of the adjuvant with the immunogenic composition. It was necessary to determine if the pain was due to the porin itself, the detergent, or a combination of the two. A study of the GC rPorB immunogenic composition in New Zealand white rabbits found no overt signs of toxicity, nor any clinically significant abnormalities in the hematology, chemistry or pathology data. Inoculation site histopathology scores did not suggest any significant adverse response due to the GC rPorB protein. Infrequent and mild reactions (edema and erythema) at the injection sites were of short duration, and were not associated with any specific antigen or adjuvant. It was necessary to employ an animal model to determine the cause of the pain in order to produce a tolerable GC rPorB immunogenic composition. Embodiments of this invention are based, in part, on the results of this study.

An animal model, the rat paw-lick (footpad) model, which has previously been employed for detection of pain associated with the injection of antibiotics, was utilized (Celozzi et al. J. Pharmacol. Methods, 1980, 4:285-189; Comerski et al., Fundamental and Appl. Toxicology, 1986, 6:335-338). This model monitors the amount of time the rats spend lifting, licking, and biting the injected paw. This model demonstrated that the detergent used to solubilize the GC rPorB, either Zwittergent® 3-12 or Zwittergent® 3-14, was responsible for the pain on injection. Similar studies have shown that the detergents octyl-glucoside and CHAPS® (3-((cholamidopropyl)dimethylammonio)-1-propane sulfonate) also cause considerable pain if present upon injection.

One of skill in the art would appreciate that other in vivo pain models or in vitro correlates of pain may be employed to determine when a pain causing immunogenic composition has been altered to a non-pain causing immunogenic composition.

However, merely identifying the cause of the problem did not presage a solution. The methods and compositions of the invention result from the further discovery that dilution or exchange of the zwitterionic detergent with a strong nonionic detergent results in a tolerable formulation that does not cause unacceptable pain responses upon injection.

Embodiments of the invention provide methods to purify hydrophobic proteins with a zwitterionic detergent, then reduce the concentration of the zwitterionic detergent to improve the tolerability of the resulting immunogenic composition. In particular, embodiments of the invention are directed to producing less painful or non-painful level subunit immunogenic compositions for injection into subjects containing a hydrophobic membrane protein.

In a specific embodiment of the invention, the hydrophobic protein is solubilized in a zwitterionic detergent such as n-Tetradecyl-N,N-dimethyl-3-ammonio-1-propanesulfonate (Zwittergent® 3-14). The term "zwitterionic detergent" refers to a detergent, which is electrically neutral overall, but has a positively charged moiety and a negatively charged moiety and is commonly used to solubilize hydrophobic proteins. Those skilled in the art will appreciate that one embodiment of this invention can also be drawn to immunogenic compositions of hydrophobic proteins initially solubilized in other zwitterionic detergents or in urea. Non-limiting examples of zwitterionic detergents include n-Octyl-N,N-dimethyl-3-ammonio-1-propanesulfonate, Zwittergent® 3-8; n-Decyl-N,N-dimethyl-3-ammonio-1-propanesulfonate, Zwittergent® 3-10; n-Dodecyl-N,N-dimethyl-3-ammonio-1-propanesulfonate, Zwittergent® 3-12; n-Tetradecyl-N,N-dimethyl-3-ammonio-1-propanesulfonate, Zwittergent® 3-14; 3-(N,N-n-Hexadecyl-N,N-dimethyl-3-ammonio-1-propanesulfonate, Zwittergent® 3-16; 3-[(3-Cholamidopropyl)dimethylammonio]-1-propanesulfonate, CHAPS®; 3-[(3-Cholamidopropyl)dimethylammonio]-2-hydroxy-1-propanesulfonate, CHAPSO®; n-Dodecyl-N,N-dimethylglycine, EMPIGEN BB®; and other zwitterionic detergents capable of causing pain in the rat footpad model.

| ZWITTERIONIC DETERGENTS | |
|---|---|
| Chemical Name | Trade Name |
| n-Octyl-N,N-dimethyl-3-ammonio-1-propanesulfonate | Zwittergent ® 3-8 |
| n-Decyl-N,N-dimethyl-3-ammonio-1-propanesulfonate | Zwittergent ® 3-10 |
| n-Dodecyl-N,N-dimethyl-3-ammonio-1-propanesulfonate | Zwittergent ® 3-12 |
| n-Tetradecyl-N,N-dimethyl-3-ammonio-1-propanesulfonate | Zwittergent ® 3-14 |
| 3-(N,N-n-Hexadecyl-N,N-dimethyl-3-ammonio-1-propanesulfonate | Zwittergent ® 3-16 |
| 3-[(3-Cholamidopropyl)dimethylammonio]-1-propanesulfonate | CHAPS ® |
| 3-[(3-Cholamidopropyl)dimethylammonio]-2-hydroxy-1-propanesulfonate, | CHAPSO ® |
| n-Dodecyl-N,N-dimethylglycine, | EMPIGEN BB ® |

One of skill in the art will appreciate that combinations of zwitterionic detergents can also be used to solubilize or refold the hydrophobic proteins of the invention from cell membranes or from inclusion bodies after recombinant expression.

In a specific embodiment of the invention, the zwitterionic detergent in the composition is diluted or exchanged with a nonionic detergent. The term "surfactant" refers to a surface active agent that can greatly reduce the surface tension of water when used in a very low concentration. The term "detergent" refers to a class of surfactants that are amphipathic molecules with a nonpolar, hydrophobic part and a polar, hydrophilic part. The terms "detergent" and "surfactant" may be used interchangeably. Detergents disrupt membranes by intercalating into phospholipid bilayers and solubilizing lipids and proteins. The hydrophobic part of a detergent molecule is attracted to hydrocarbons, while the hydrophilic part is strongly attracted to water. Some detergents are natural products, but most are synthetic molecules developed for cleaning and for dispersing mixtures of oil and water. The polar (hydrophilic) ends of detergents can be either charged (ionic), as in the case of sodium dodecyl sulfate (SDS), or uncharged (nonionic), as in the case of the Triton® detergents or can have a positively charged moiety and a negatively charged moiety as in the case of zwitterionic detergents.

The term "nonionic detergent" refers to a molecule acting as a detergent which is uncharged. The hydrophilic group is made up of some other very water-soluble moiety, e.g., a short, water-soluble polymer chain, rather than a charged species. Traditionally, nonionic detergents have used poly (ethylene oxide) chains as the hydrophilic group. Poly(ethylene oxide) is a water soluble polymer; the polymers used in nonionic detergents are typically 10 to 100 monomer units long. The two common classes of detergents that use poly (ethylene oxide) chains as their hydrophilic group are the alcohol ethoxylates and the alkylphenol ethoxylates. Those skilled in the art will appreciate that one embodiment of this invention can be drawn to compositions diluted or exchanged with other nonionic detergents. Non-limiting examples of nonionic detergents include: N,N-bis(3-D-glucon-amidopropyl)cholamide, BigCHAP®; alpha-[4-(1,1,3,3-tetramethyl-butyl)phenyl]-omega-hydroxypoly(oxy-1,2-ethanediyl), Triton® X-100; Polyoxyethylene (20) sorbitan monolaurate, TWEEN® 20™; Polyoxyethylene (20) sorbitan monooleate, TWEEN 80; Polyoxyethylene (35) Lauryl Ether, BRIJ® 35; Ethylphenolpoly(ethyleneglycolether)$_{11}$, Nonidet P40, NP40; n-Octyl-b-D-glucopyranoside, OG; and other nonionic detergents capable of solubilizing hydrophobic proteins. One of skill in the art will appreciate that combinations of nonionic detergents can also be used to solubilize the hydrophobic proteins and reduce the pain associated with administering such proteins in immunogenic compositions.

| NONIONIC DETERGENTS | |
|---|---|
| Chemical Name | Trade Name |
| alpha-[4-(1,1,3,3-tetramethylbutyl)phenyl]-omega-hydroxypoly(oxy-1,2-ethanediyl) | TRITON ® X-100 |
| Polyoxyethylene (20) sorbitan monolaurate | TWEEN ® 20 ™ |
| Polyoxyethylene (20) sorbitan monooleate | TWEEN ® 80 ™ |
| Polyoxyethylene (35) Lauryl Ether | BRIJ ® 35 |
| N,N-bis(3-D-glucon-amidopropyl)cholamide | BigCHAP ® |
| Octylphenoxypolyethoxyethanol and Polyethyleneglycol-p-isooctylphenyl Ether | Nonidet P40 |
| Decanoyl-N-methylglucamide | MEGA 10 ® |
| n-Octyl-b-D-glucopyranoside | OG |
| n-Dodecyl-beta-D-maltoside | |

The term "hydrophobic" as used herein refers to the tendency of certain substances to repel water, or to tend not to combine with water or to be incapable of dissolving in water. The term "hydrophilic" as used herein refers to the tendency of certain substances to be attracted to water, or to dissolve in water. The term "hydrophobic protein" refers to a protein which is insoluble or only slightly soluble in water. Hydrophobic proteins generally display minimal association with water and water-soluble ionic compounds, they instead associate with each other or other lipids outside of the aqueous phase.

The term "composition" refers to an aqueous medium or solution for the preservation or administration, or both, of that medium or solution, which is preferably directly administered to a subject. The composition of one embodiment of the invention can comprise protein, a zwitterionic detergent, and a nonionic detergent. Compositions can be characterized by their functions, such as immunogenic, therapeutic, or diagnostic compositions.

The term "immunogenic composition," broadly refers to any composition that may be administered to elicit an immunogenic response against an antigen present in the composition. The immunogenic composition of one embodiment of the invention can comprise an antigenic protein or polypeptide, a zwitterionic detergent, a nonionic detergent, and ionic detergents. An immunogenic composition may be used as either a prophylactic or as a treatment in the recipient. An immunogenic composition generally comprises an immunologically effective dose of an immunogen (e.g., an antigen of an infectious agent) and a pharmaceutically acceptable carrier and, optionally, an adjuvant.

As defined herein, "isolated" means that the protein or polypeptide was obtained from and separated from a particular source. For example, "isolated from *N. meningitidis*" means that the protein or polypeptide was obtained from and separated from *N. meningitidis* bacterial cells. An isolated material may be, but need not be, purified.

As defined herein, "purified" refers to that the protein or polypeptide of interest has been substantially separated from the various other protein, lipid, nucleic acid, and carbohydrate components that naturally occur with the polypeptide. Whatever residual amounts of foreign components are present do not interfere with the use of the purified material in an immunogenic composition or as an antigen. The term "purified" is not intended to exclude synthetic polypeptide preparations retaining artifacts of their synthesis; nor is the term meant to exclude preparations that include some impurities, so long as the preparation exhibits reproducible protein or polypeptide characterization data, for example molecular weight, sugar residue content, chromatographic response, and immunogenic behavior. Such characteristics can be evaluated by chromatography, gel electrophoresis, immunoassay, composition analysis, mass spectroscopy, or biological assay, and other methods known in the art.

Methods for purification are well-known in the art. For example, polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the protein of polypeptide in a recombinant system in which the expressed protein or polypeptide contains an additional sequence tag that facilitates purification, such as, but not limited to, a polyhistidine sequence, or a sequence that specifically binds to an antibody, such as FLAG and GST. The protein or polypeptide can then be purified from a crude lysate of the host cell by chromatography on an appropriate solid-phase matrix. Alternatively, antibodies produced against the protein or against peptides derived therefrom can be used as purification reagents. Cells are purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting [FACS]). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

As used herein, the term "about" or "approximately" means within 50% or a given value, preferably within 20%, more preferably within 10%, more preferably still within 5%, and most preferably within 1% of a given value. Alternatively, the term "about" or "approximately" means that a value can fall within a scientifically acceptable error range for that type of value, which will depend on how qualitative a measurement can be given the available tools. "About" or "approximately" define a distribution around a mean value. Unless otherwise stated, all values are approximate, and implicitly fall within an error range.

Altering Detergent Composition

Embodiments of the present invention provide methods for preparing and administering immunogenic compositions comprising a hydrophobic protein. The methods involve solubilizing or refolding the hydrophobic protein with a zwitterionic detergent solution. Certain embodiments of the invention provide for altering the detergent composition of the hydrophobic protein solution with a nonionic detergent, such that the altered composition produces a reduction in pain as measured in the rat footpad model as compared to the unaltered composition. As used herein, "altering" refers to the process of improving the tolerability of an immunogenic composition by one of the following methods: (i) diluting the zwitterionic detergent, (ii) exchanging the zwitterionic detergent with a non-pain causing nonionic detergent, or (iii) adding a non-pain causing nonionic detergent but keeping the concentration of the zwitterionic detergent constant.

One embodiment of the present invention provides a method for preparing immunogenic compositions comprised of hydrophobic proteins. In one embodiment of the invention, the method involves solubilizing the protein with a zwitterionic detergent, then diluting the zwitterionic detergent with a nonionic detergent to decrease the concentration of the zwitterionic detergent. In one embodiment of the invention, the zwitterionic detergent is diluted at least a factor of about 2, for example from about 0.05% to about 0.025%. In another embodiment of the invention, the zwitterionic detergent is diluted at least a factor of about 4, for example from about 0.05% to about 0.02%. In another embodiment of the invention, the zwitterionic detergent is diluted at least a factor of about 5, for example from about 0.05% to about 0.01%. In a particular embodiment of the invention, the zwitterionic detergent is diluted at least a factor of about 7.5, for example from about 0.05% to about 0.067%. In one embodiment of the invention, the zwitterionic detergent is diluted at least a factor of about 10, for example from 0.05% to about 0.005%. In another embodiment of the invention, the zwitterionic detergent is diluted at least a factor of about 15, for example from 0.05% to about 0.03%. In one embodiment of the invention, the zwitterionic detergent is diluted at least a factor of about 20, for example from 0.05% to about 0.0025%. One of skill in the art will appreciate that the as the dilution factor increases, the process of dilution begins to become an exchange process. Because zwitterionic detergents can cause pain upon injection, reducing the concentration of these detergents, especially to levels below their critical micelle concentration, results in a composition which is less painful upon administration. Those skilled in the art will appreciate the advantage of non-painful or less painful immunogenic compositions comprised of hydrophobic proteins, especially hydrophobic membrane proteins such as porins.

In one embodiment of the invention, the less painful or non-pain causing detergent is added to a level that is sufficient to maintain the solubility of the hydrophobic protein while the concentration of the pain causing detergent is kept constant. In another embodiment of the invention, the less painful or nonpain causing detergent is added to a level that is above its critical micelle concentration while the concentration of the pain causing detergent is kept constant. While not intending to be bound by any particular theory, it is believed that adding the non-painful detergent to the pain causing detergent results in mixed micelles with the pain causing detergent and non-pain causing detergent and results in reduction or elimination in pain (improved tolerability) induced upon injection. See Example 8.

An alternative method for preparing an immunogenic composition of one embodiment of the invention involves solubilizing the protein with a zwitterionic detergent, then exchanging the zwitterionic detergent for a nonionic detergent. Methods for exchanging the detergent are known in the art. One such technique is ion exchange chromatography. In ion exchange chromatography the protein is first solubilized in a solution containing a zwitterionic detergent. The solubilized protein is then loaded onto an ion exchange column, such as a Q-Sepharose™ column (Amersham Pharmacia Biotech, Piscataway, N.J.) that has been equilibrated in the same buffer. The bound protein is washed with a solution containing an acceptable nonionic detergent. The protein is eluted using a linear gradient of a saline solution containing the nonionic detergent. The eluted material is then dialyzed and passed through a 0.22 μm membrane filter and the protein concentration of the filtered material is determined. One of skill in the art will appreciate that other exchange techniques known in the art can be used to exchange the pain causing detergent for the non pain causing detergent. Such techniques include for example membrane dialyisis and gel filtration chromatography.

In an embodiment of the invention, the zwitterionic detergent is a ZWITTERGENT® detergent such as ZWITTERGENT® 3-8; ZWITTERGENT® 3-10; ZWITTERGENT® 3-12; ZWITTERGENT® 3-14; or ZWITTERGENT® 3-16 detergent.

In a specific embodiment of the present invention, the protein solubilized in a zwitterionic detergent is either diluted with or exchanged with the nonionic detergent polyethylene glycol tert-octylphenylether (TRITON® X-100). Those skilled in the art will appreciate that an embodiment of this invention can also be drawn to immunogenic compositions of hydrophobic proteins solubilized in a zwitterionic detergent, which are diluted or exchanged with another nonionic detergent. In a specific embodiment, the final concentration of polyethylene glycol tert-octylphenylether is about 0.01% to about 0.2%. In another embodiment, the final concentration of polyethylene glycol tert-octylphenylether is about 0.05%.

An embodiment of the present invention provides for a composition that contains a zwitterionic detergent which is diluted or exchanged so that the final concentration is reduced, resulting in a composition which will cause less pain compared to the undiluted or unexchanged composition. The reduction in pain can be determined by the rat footpad pain test. In a specific embodiment of the invention, pain is reduced by at least 50% as measured by the rat footpad pain test. In another specific embodiment of the invention, the zwitterionic detergent is reduced to a concentration below its critical micelle concentration.

As used herein, the term "pain" refers to a sensation of discomfort. Pain is associated with actual or potential injury or tissue damage due to inflammation, ischemia, mechanical or other irritation. The nervous system receives input from a large number of sensory receptors. The sensory and motor neurons of circuits are contained within the peripheral nervous system. These circuits send information to and receive information from the central nervous system (CNS), which comprises the brain and spinal cord and is composed mainly of interneurons. Highly specialized sensory receptor cells, which respond to specific environmental stimuli, send their outputs either directly to the brain (e.g., taste and odorant receptors) or to peripheral sensory neurons (e.g., pain and stretching receptors). The term "nociception" as used herein refers to the neural mechanisms by which noxious stimuli are detected. Nociception involves two steps: transductions of noxious stimuli by peripheral nerve endings and transmission of these signals to pain-sensitive (nociceptive) neurons of the central nervous system.

The "rat footpad pain" or "rat paw-lick" test or model as used herein refers to a test or model used to determine the pain induced by a specific formulation upon injection. The test consists of uniformly injecting into the footpad of rats of the same species and approximately the same weights compositions to be assessed as pain causing agents along with compositions known to cause pain at the injection site, as well as compositions known not to cause pain at the injection site. A statistically significant number of animals are to be used for each test and control formulation. After the injection, the animal is placed in a cage with mirrors and then observed by a technician (preferably blinded as to the identity of the immunogenic composition) for 20 to 30 minutes for flinching, lifting, licking, or biting of the injected paw. The amount of time spent on these pain response behaviors are recorded using a stopwatch and summed for 10 minute periods.

The phrase "less painful" as used herein refers to an alteration in the composition that leads to a reduction in the length of time or intensity, or both, of a pain response compared to that of the non-altered composition as measured by the rat footpad pain test. The phrase "50% reduction in pain" as used herein refers to a 50% reduction in the amount of time spent on pain responses as measured by the rat footpad pain test when comparing altered and unaltered immunogenic compositions administered in equal injection volumes by the same means and observed for the same length of time. The number of animals in each group is a statistically significant number. Observation of the different injection groups is preferably done by the same technician and who is blinded as to the identification of the compositions.

The term "critical micelle concentration (CMC)" as used herein refers to the concentration of a specific detergent above which monomers of detergent molecules cluster to form micelles. The concentration units are often given in either millimolar of percent (V/V). See *The Hydrophobic Effect: Formation Of Micelles And Biological Membranes* by Charles Tanford John Wiley & Sons New York (Second Edition, 1980). At very low concentrations, detergents dissolve in pure water as isolated molecules. As the concentration increases, due to the hydrophobic effect, the molecules begin to form micelles. These are small, spherical aggregates in which hydrophilic parts of the molecules face outward and the hydrophobic parts cluster in the center. The CMC at which micelles form is characteristic of each detergent and is a function of the structures of its hydrophobic and hydrophilic parts. One of skill in the art would appreciate that the values of CMC are often stated as a range of values because such values are dependent on temperature, pressure etc. Some of the known critical micelle concentrations are listed below:

| Detergent | CMC (%) | CMC (mM) |
| --- | --- | --- |
| Zwittergent ® 3-8 | 4.6-10.9 | 330 |
| Zwittergent ® 3-10 | 0.43-1.23 | 25-40 |
| Zwittergent ® 3-12 | 0.047-0.13 | 2-4 |
| Zwittergent ® 3-14 | 0.004-0.015 | 0.1-0.4 |
| CHAPS ® | 0.18-0.62 | 6-10 |
| BigCHAP ® | 0.3 | 3-4 |
| EMPIGEN BB ® | 0.054 | 1.6-2.1 |
| TRITON ® X-100 | 0.013-0.056 | 0.2-0.9 |
| TWEEN 80 | 0.0016 | 0.012 |
| BRIJ | 0.011 | 0.09 |

Mixed micelles containing mixtures of detergent molecules readily form because the driving force for association of amphipathic molecules into micelles is nonspecific and because the resultant micelle has a liquid like core. As used herein "mixed micelles" refers to micelles containing mixtures of different detergent molecules, such as mixed micelles of Zw 3-12 and TX-100.

Proteins and Antigens

The term "antigen" refers to any substance that can be recognized by the immune system and upon such recognition will result in a specific immune response, generally resulting in the production of specific antibodies or cellular immunity. While the term antigen can include whole bacteria or virus, immunogenic compositions often contain subunit antigens such as proteins or peptides from the pathogens. Subunit antigens can be derived from any type of infectious agent such as bacteria, viruses, parasites, fungi, or tumor cells.

Many bacteria, including *E. coli*, have an outer membrane surrounding their plasma membrane. The outer membrane is penetrated by various pore-forming porin proteins, which allow selected hydrophilic solutes of up to 600 Daltons to diffuse across the outer lipid bilayer. Porins are pore-forming transmembrane proteins that cross the lipid bilayer and have a β-barrel-type protein structure. Some multipass transmembrane proteins have their transmembrane segments arranged as a closed β-sheet (a β-barrel) rather than as α helices. The barrel is formed from a 16-stranded antiparallel β-sheet, which is sufficiently curved to roll up into a cylindrical structure. Polar side chains line the aqueous channel on the inside, while nonpolar side chains project from the outside of the barrel to interact with the hydrophobic core of the lipid bilayer. The best studied examples of such proteins are the porins, which are found in the outer membrane of many bacteria. They are among the few transmembrane proteins whose complete atomic structure has been solved by X-ray crystallography.

An exemplary embodiment of the present invention provides for an immunogenic composition in which the antigen is a porin. Those of ordinary skill in the art appreciate that certain porins are considered good immunogenic composition candidates. For example, Porin (Por) A is a subcapsular protein antigen of group B *N. meningitidis* that induces antibody formation upon natural infection (Lehmann, A. K., et al., *Infect. Immun.*, 1999, 67:2552.), and is considered a good meningococcal immunogenic composition candidate (van der Voort, E. R., et al., *Vaccine*, 2000, 18:1334). Because of the Por proteins' presence at the bacterial cell surface of *Neisseria meningitidis* and *Neisseria gonorrhoeae*, their comparatively conserved nature, and their abundance in the outer membrane, Por proteins have gained much attention as potential immunogenic composition candidate antigens. See Heckels, J. E., et al., *Vaccine*, 8:225-230 (1990). Molecular epidemiology studies suggest that Por-specific antibodies that develop during the natural infection may provide partial protection against reinfection with gonococci of the same Por serotype (Plummer, F. A., et al., *J. Clin. Invest*, 1989, 83:1472-1476). On the basis of structural and immunochemical characteristics, two major subtypes of Por proteins have been recognized, termed PorA and PorB, which are encoded by the mutually exclusive alleles. Those of ordinary skill in the art appreciate that it is important to produce non-painful or less-painful immunogenic compositions comprising hydrophobic membrane proteins, including gonococcal and meningococcal porins to be administered to mammals.

*E coli* strain BL21 (DE3) harboring plasmid pUNC7 containing the PIA gene has been deposited on Nov. 13, 1987 with the Northern Regional Research Laboratory (NRRL) under accession No. NRRL #B-18263. *E coli* strain BL21 (DE3) harboring plasmid pUNCH25 containing the PIB gene has been deposited with the American Type Culture Collection under Accession No. 67775.

"Membrane proteins" are proteins that are associated with membranes. Different membrane proteins are associated with membranes in different ways. Many membrane proteins extend through the lipid bilayer, with part of their mass on either side. Like their lipid neighbors, these transmembrane proteins are amphipathic, having regions that are hydrophobic and other regions that are hydrophilic. Their hydrophobic regions pass through the membrane and interact with the hydrophobic tails of the lipid molecules in the interior of the bilayer. Their hydrophilic regions are exposed to water on one or the other side of the membrane. The hydrophobicity of some of these membrane proteins is increased by the covalent attachment of a fatty acid chain that is inserted into membrane leaflets of the lipid bilayer. Other membrane proteins are located entirely in the cytosol or in the periplasmic space and are associated with the bilayer only by means of one or more covalently attached fatty acid chains or other types of lipid chains. Yet other membrane proteins are entirely exposed at the external cell surface of eucaryotic cells or the outer membrane of gram negative bacterial cells, being attached to the bilayer only by a covalent linkage.

Some proteins that do not extend into the hydrophobic interior of the lipid bilayer at all are bound to one or the other face of the membrane by noncovalent interactions with other membrane proteins. Many of these can be released from the membrane by relatively gentle extraction procedures, such as exposure to solutions of very high or low ionic strength or extreme pH, which interfere with protein-protein interactions but leave the lipid bilayer intact; these proteins are referred to operationally as "peripheral membrane proteins." By contrast, transmembrane proteins, many proteins held in the bilayer by lipid groups, and some other tightly bound proteins cannot be released in these ways and therefore are called "integral membrane proteins." In general, transmembrane proteins (and some other tightly bound membrane proteins)

can be solubilized only by agents that disrupt hydrophobic associations and destroy the lipid bilayer, such as zwitterionic detergents.

One of skill in the art will appreciate that the hydrophobic proteins of the invention may be produced by recombinant DNA methods and expressed in either bacteria or in eucaryotic cells using methods known in the art. It will also be appreciated that the hydrophobic proteins may initially be recovered from inclusion bodies using urea or guanidine to solubilize the individual protein molecules. The solubilized (but denatured) protein is then refolded by transfer through exchange or dilution to a solution containing a zwitterionic detergent or a combination of zwitterionic detergents or a combination of zwitterionic detergents and other detergents.

Compositions and Methods of Treatment

Embodiments of the invention provide for the immunogenic compositions to be administered to animals for immunotherapy or immunoprophylaxis, or for other therapeutic or diagnostic purposes. The compositions can be administered by injection or other routes of administration without eliciting an unacceptable pain response. The immunogenic compositions can include an adjuvant and/or a carrier. Embodiments of the invention also provide for an immunologically effective dose of the composition to be administered to prevent or treat a specific disease. For example, compositions can be administered for the prevention or treatment of gonorrhea or meningitis or any gram negative bacterial disease.

In one embodiment of the invention, the immunogenic compositions are administered to a mammal. The term "mammal" as used herein is defined as the group of species within the class mammalian. Non-limiting examples of mammals are agricultural animals such as sheep, pigs and cattle, rodents such as rats and mice, and primates such as monkeys, apes and humans.

The term "immunologically effective dose" refers to that amount of a compound or composition that is sufficient to elicit a desired immune response. In general, selection of the appropriate immunologically effective amount or dosage for the immunogenic compositions of embodiments of the present invention will also be based upon the particular immunogenic composition employed, as well as the physical condition of the subject, most especially including the general health and weight of the immunized subject. Such selection and upward or downward adjustment of the effective dose is within the skill of the art. The amount of active component required to induce an immune response without significant adverse side effects varies depending upon the composition employed.

In certain embodiments, the immunogenic composition will comprise one or more adjuvants. As used herein, an "adjuvant" is a substance that serves to enhance the immunogenicity of an immunogenic composition of particular embodiments of the invention.

A number of cytokines or lymphokines have been shown to have immune modulating activity, and thus may be used as adjuvants, including, but not limited to, the interleukins 1-α, 1-β, 2, 4, 5, 6, 7, 8, 10, 12 (see, e.g., U.S. Pat. No. 5,723,127), 13, 14, 15, 16, 17 and 18 (and its mutant forms), the interferons-α, β and γ, granulocyte-macrophage colony stimulating factor (see, e.g., U.S. Pat. No. 5,078,996 and ATCC Accession Number 39900), macrophage colony stimulating factor, granulocyte colony stimulating factor, GSF, and the tumor necrosis factors α and β. Still other adjuvants useful in particular embodiments of the invention include a chemokine, including without limitation, MCP-1, MIP-1α, MIP-1β, and RANTES. Adhesion molecules, such as a selectin, e.g., L-selectin, P-selectin and E-selectin may also be useful as adjuvants. Still other useful adjuvants include, without limitation, a mucin-like molecule, e.g., CD34, GlyCAM-1 and MadCAM-1, a member of the integrin family such as LFA-1, VLA-1, Mac-1 and p150.95, a member of the immunoglobulin superfamily such as PECAM, ICAMs, e.g., ICAM-1, ICAM-2 and ICAM-3, CD2 and LFA-3, co-stimulatory molecules such as CD40 and CD40L, growth factors including vascular growth factor, nerve growth factor, fibroblast growth factor, epidermal growth factor, B7.2, PDGF, BL-1, and vascular endothelial growth factor, receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6. Still another adjuvant molecule includes Caspase (ICE). See, also International Patent Publication Nos. WO 98/17799 and WO 99/43839, the disclosures of which are incorporated herein by reference in their entirety.

Suitable adjuvants used to enhance an immune response further include, without limitation, MPL® (3-O-deacylated monophosphoryl lipid A; Corixa, Hamilton, Mont.), which is described in U.S. Pat. No. 4,912,094, which is hereby incorporated by reference. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918, which is hereby incorporated by reference. One such AGP is 2-[(R)-3-Tetradecanoyloxytetradecanoylamino]ethyl 2-Deoxy-4-O-phosphono-3-O—[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form or as a stable emulsion.

Still other adjuvants include mineral oil and water emulsions, aluminum salts (alum), such as aluminum hydroxide, aluminum phosphate, etc., Amphigen, Avridine, L121/squalene, D-lactide-polylactide/glycoside, pluronic polyols, muramyl dipeptide, killed Bordetella, saponins, such as Stimulon® QS-21 (Antigenics, Framingham, Mass.), described in U.S. Pat. No. 5,057,540, which is hereby incorporated by reference, and particles generated therefrom such as ISCOMS (immunostimulating complexes), *Mycobacterium tuberculosis*, bacterial lipopolysaccharides, synthetic polynucleotides such as oligonucleotides containing a CpG motif (U.S. Pat. No. 6,207,646, which is hereby incorporated by reference), a pertussis toxin (PT), or an *E. coli* heat-labile toxin (LT), particularly LT-K63, LT-R72, PT-K9/G129; see, e.g., International Patent Publication Nos. WO 93/13302 and WO 92/19265, incorporated herein by reference.

Also useful as adjuvants are cholera toxins and mutants hereof, including those described in published International Patent Application number WO 00/18434 (wherein the glutamic acid at amino acid position 29 is replaced by another amino acid (other than aspartic acid), preferably a histidine). Similar CT toxins or mutants are described in published International Patent Application number WO 02/098368 (wherein the isoleucine at amino acid position 16 is replaced by another amino acid, either alone or in combination with the replacement of the serine at amino acid position 68 by another amino acid; and/or wherein the valine at amino acid position 72 is replaced by another amino acid). Other CT toxins are described in published International Patent Application number WO 02/098369 (wherein the arginine at amino acid position 25 is replaced by another amino acid; and/or an amino acid is inserted at amino acid position 49; and/or two amino acids are inserted at amino acid positions 35 and 36).

A variety of administration routes are available. The particular mode selected will depend, of course, upon the particular immunogenic composition selected, the particular condition being treated, and the dosage required for therapeutic efficacy. The methods of certain embodiments of this invention, generally speaking, can be practiced using any mode of administration that is medically acceptable, meaning any mode that produces effective levels of an immune response without causing clinically unacceptable adverse effects. Examples of routes of administration include, but are not limited to, parenteral (e.g., intravenous, intra-arterial, intradermal, transdermal, intramuscular, subcutaneous, intraperitoneal), transmucosal (e.g., oral, rectal, intranasal, vaginal, respiratory) and transdermal (topical).

The preferred method of administration of the immunogenic composition is parenteral administration. Solutions or suspensions used for parenteral administration include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

The phrase "pharmaceutically acceptable" refers to molecular entities and compositions that are physiologically tolerable and do not typically produce an allergic or similar untoward reaction (for example, gastric upset, dizziness and the like) when administered to an individual. Preferably, and particularly where an immunogenic composition is used in humans, the term "pharmaceutically acceptable" may mean approved by a regulatory agency (for example, the U.S. Food and Drug Agency) or listed in a generally recognized pharmacopeia for use in humans or animals (for example, the U.S. Pharmacopeia).

The term "carrier" refers to a diluent, adjuvant, excipient, or vehicle with which a compound is administered. Sterile water or aqueous saline solutions and aqueous dextrose and glycerol solutions are preferably employed as carriers, particularly for injectable solutions. Exemplary suitable pharmaceutical carriers are described in "Remington's Pharmaceutical Sciences" by E. W. Martin. The appropriate carrier will be evident to those skilled in the art and will depend in large part upon the route of administration.

Toxicity and therapeutic efficacy of compounds can be determined by standard pharmaceutical procedures, for example in cell culture assays or using experimental animals to determine the LD50 and ED50. The parameters LD50 and ED50 are well known in the art, and refer to the doses of a compound which are lethal to 50% of a population and therapeutically effective in 50% of a population, respectively. The dose ratio between toxic and therapeutic effects is referred to as the therapeutic index and may be expressed as the ratio: LD50/ED50. Compounds that exhibit large therapeutic indices are preferred. While compounds that exhibit toxic side effects may be used, in such instances it is particularly preferable to use delivery systems that specifically target such compounds to the site of affected tissue so as to minimize potential damage to other cells, tissues or organs and to reduce side effects.

EXAMPLES

Embodiments of the present invention are described by way of the following examples. However, the use of these or other examples anywhere in the specification is illustrative only and in no way limits the scope and meaning of the invention or any exemplified term. Likewise, the invention is not limited to any particular embodiment described herein. Indeed, many modifications and variations of the invention may be apparent to those skilled in the art upon reading this specification and can be made without departing from its spirit and scope.

Abbreviations

The following abbreviations were used throughout the examples:

Zw—Zwittergent 3-14; 0.1×Zw=0.005% Zw 3-14; 1×Zw=0.05% Zw 3-14.

TX—TRITON X-100; reduced TRITON® X-100 ("red TX")

GC PorB—recombinant gonococcal PorB (from strain FA1090)

Mn PorA—recombinant meningococcal PorA (Class I porin)

0.1×PorB=10 µg/ml GC rPorB; 1×PorB=100 µg/ml GC rPorB;

Example 1

Pain Responses to Injection of Various Immunogenic Compositions

Materials and Methods

Immunogenic composition preparation. Recombinant gonococcal PorB ("GC rPorB" from *N. gonorrhoeae* strain FA1090) was produced in *E. coli* using the pET-17b expression vector (Novagen, Inc., Madison, Wis.). The recombinant protein, which was expressed in inclusion bodies, was solubilized in urea and purified by column chromatography in Zwittergent® ("Zw") 3-14 under current good manufacturing practice (cGMP). The batch concentrate material was stored in 10 mM $NaPO_4$ (pH 7.4), 150 mM NaCl and 0.05% (w/v) Zw 3-14 (Calbiochem, San Diego, Calif.; cat. #693017) at −20° C. The protein concentration of this material was 1.3 mg/ml.

All buffers used in the immunogenic compositions tested in the rat footpad pain model were prepared using water for injection ("WFI") and were passed through a 0.22 µm membrane filter. Reduced TRITON® X-100 ("red TX") was obtained from Sigma (St. Louis, Mo.; cat. #X-100R-PC), formalin was obtained from EM Sciences (Gibbstown, N.J.; cat #FX0415-5), and all other reagents were obtained from J. T. Baker (Phillipsburg, N.J.) including TRITON® X-100 ("TX") (cat. #X198-05). For the experiments shown in Example 1, the PBS, not pyrogen-free, was obtained from Sigma (cat. #P0261). For the remaining examples, pyrogen-free PBS was prepared.

The following clinical grade immunogenic compositions were used in these studies:

1) GC rPorB containing 100 µg/ml recombinant gonococcal porin protein in PBS (pH 7.2) containing 0.05% (w/v) Zw 3-14;

2) Non-typable *Haemophilus influenzae/Moraxella catarrhalis* ("NTHi/Mcat") immunogenic composition containing 50 µg each of the following: recombinant P4 and recombinant P6 proteins derived from *Haemophilus influenzae* and 50 µg of native UspA2 (*M. catarrhalis*) in PBS (pH 7.2) containing 0.04% (v/v) TX (with or without 250 µg/ml aluminum as $AlPO_4$), 0.03% (w/v) Zw 3-12. [This immunogenic composition has not been associated with pain on injection in human volunteers, presumably because 0.03% Zw 3-12 is below the critical micelle concentration of this detergent. In contrast the 0.04% TX concentration is above the CMC for TX.] and 3) 100 µg/ml of purified F protein from respiratory syncytial virus ("PFP-2") in PBS (pH 6.5) containing 100 µg/ml STIMULON® QS-21 (Antigenics, Framingham), which has been associated with immediate pain on injection in human volunteers.

Pain Control: Formalin (formaldehyde 100 µl) was also used as a positive pain control because injection of a 5% formalin solution results in a two-phase pain response, one immediate and one delayed.

The experimental immunogenic compositions for the rat footpad studies were prepared by aseptically diluting the protein with the appropriate buffer, either PBS (pH 7.2) or 10 mM Tris (pH 7.5), 150 mM NaCl ("TBS") containing Zw 3-14, TX, or reduced TX as indicated, in a laminar flow hood. The positive control for these experiments was 5% (v/v) formalin in PBS (pH 7.2). The immunogenic compositions were dispensed into 2 ml, Type 1 glass vials, sealed with West latex-free stoppers and an aluminum seal. All immunogenic compositions were stored at 2-8° C.

Rat footpad pain testing. The immunogenic composition samples were brought to room temperature prior to being administered to the animals. The animals were injected by a technician who was not involved in the monitoring of pain responses. Male Sprague Dawley rats (Crl:CD®(SD)IGS BR, 50-100 g at arrival) from Charles River Laboratories Inc. (Kingston, N.Y.) were used for all studies. The rats were acclimated at the research facility for approximately one week prior to initiation of a study, at which point they weighed 100-150 g. The paw to be injected was examined prior to injection to verify absence of any injury. The animal was then restrained in the technician's arm such that the hind legs extended forward. The right rear leg was grasped just above the hock joint and pressure was exerted to hold the paw straight out, with plantar (sole) facing upwards. Using a new 23 gauge needle for each animal, the operator inserted the bevel side up in the center of paw, parallel to the surface of the paw, until the needle was in the center of the pad. The material was then injected and the needle left in place for 3-5 seconds prior to withdrawal, to minimize leakage from the injection site. The injection volumes were 0.1 ml.

The animal was then placed in a cage with 3 mirrors (adjoining sides and floor) and observed by a different technician (blinded as to the identity of the immunogenic composition) for 30 minutes for flinching, lifting, licking, or biting of the injected paw. The length of time spent on these pain response behaviors was recorded using a stopwatch and summed for 10 minute periods. There were six animals per group.

Statistical Analysis. Results were analyzed using an ANOVA method adjusting for multiple comparisons that compared each treatment group with control group who received buffer alone (either PBS or TBS). This is a conservative approach because the variance of the measurements in these studies differed greatly between groups. Furthermore the assumption of normality is not satisfied. Because of these concerns, a rank-transformation was applied to the data before using the ANOVA method.

Secondary analyses comparing individual immunogenic compositions were done using the Wilcoxon rank test. The Bonferroni multiple comparison adjustment was performed when appropriate. These secondary analyses included comparisons of (a) GC rPorB/Zw 3-14 diluted into TX or reduced TX containing buffers, (b) 10 µg/ml or 100 µg/ml GC rPorB in 0.05% Zw 3-14, (c) 10 µg/ml or 100 µg/ml GC rPorB in 0.05% Zw 3-14 with the NTHi/Mcat immunogenic composition and (d) PBS with either 0.05% or 0.005% Zw 3-14.

A 0.05 $\alpha$-level of significance was used for each study in the primary analyses concerned with the comparisons to a negative control immunogenic composition and another 0.05 $\alpha$-level of significance was used for each study considered under the secondary analyses. A Bonferroni adjustment for multiple comparisons was used.

Results

Table 1 summarizes the amount of time spent on pain responses to 0.1 ml injection of various immunogenic compositions during sequential 10 minute intervals. PBS and the non-typeable *Haemophilus influenza/Moraxella catarrhalis* (NTHi/Mcat) were used as negative controls. PBS+Zw 3-14, PFP from respiratory syncytial virus+QS-21 adjuvant (Antigenics, New York, N.Y.), GC rPorB in PBS+0.05% Zw 3-14 were test groups. 5% formalin was used as a positive control for pain on injection. The median, mean and range are given for each immunogenic composition group for each post-treatment period of observation. There were 6 animal in every group. Table 2 summarizes the statistical analyses of the results given in Table 1. The p-values reported are the results from the rank-transform ANOVA approach. The statistical tests were confirmed by the Steel and Dwaas method.

Clearly formalin induced the highest pain response among the compositions tested, as shown in Tables 1 and 2. The interpretation of the data from this study was complicated because the PBS used as the buffer control in this study (obtained from Sigma) was not pyrogen free and therefore probably caused greater than expected pain responses. Nonetheless, the data suggest that the pain responses induced by 100 µg/ml of GC rPorB, 0.05% Zw 3-14 in PBS, or PFP-2+QS-21 during the first ten minutes post immunization were greater than the NTHi/Mcat immunogenic composition, although these differences were not statistically significant.

TABLE 1

Pain Responses in Seconds to Injection of 0.1 ml Injection of Various Immunogenic Compositions.

| Immunogenic Composition | Time pain response (sec) | | | | | |
|---|---|---|---|---|---|---|
| | 0-10 min. | | 10-20 min. | | 20-30 min. | |
| | Median | Mean (range) | Median | Mean (range) | Median | Mean (range) |
| PBS | 11 | 16 (0-43) | 7 | 16 (0-44) | 0 | 11 (0-64) |
| PBS + 0.05% Zw 3-14 | 2 | 36 (0-144) | 19 | 30 (0-86) | 1 | 16 (0-77) |
| PFP2 + QS-21 | 20 | 41 (0-103) | 7 | 19 (0-62) | 27 | 33 (0-74) |
| GC rPorB in PBS + 0.05% Zw 3-14 | 47 | 46 (7-89) | 34 | 37 (2-81) | 18 | 16 (0-34) |
| NTHi/Mcat | 0 | 2 (0-7) | 0 | 3 (0-15) | 0 | 4 (0-21) |
| 5% Formalin | 311 | 274 (78-381) | 292 | 312 (171-461) | 448 | 450 (376-548) |

TABLE 2

Statistical Analyses of Table 1 ($\alpha$-level = 0.05/5 = 0.01).

| Immunogenic Composition Compared with PBS alone | 0-10 min. | 10-20 min. |
|---|---|---|
| PBS + 0.05% Zw 3-14 | 0.5651 | 0.2385 |
| PFP-2 + QS-21 | 0.9366 | 0.5192 |
| GC rPorB in PBS + 0.05% Zw 3-14 | 0.1591 | 0.0597 |
| NTHi/Mcat | 0.0269 | 0.1526 |
| 5% Formalin | 0.0005 | <0.0001 |

In the next example, the volume of the immunogenic compositions was doubled to a 200 μl injection volume in an to attempt to increase the overall sensitivity of the method.

Example 2

Effect of Injection Volume on Pain Responses

Materials and Methods

Immunogenic composition preparation. Immunogenic compositions were prepared as described in Example 1. To increase the sensitivity of this model, the maximum injection volume for this model (0.2 ml) was evaluated. In this example, the PBS was pyrogen-free.

Rat footpad pain testing. Rat footpad pain testing was performed as described in Example 1. In this example four to six animals were in each group, and 0.1 ml and 0.2 ml injection volumes were used.

Statistical analysis. Statistical analysis was performed as described in Example 1.

Results

Table 3 summarizes the effect of injection volume (0.1 ml compared to 0.2 ml) on pain responses. The median, mean and range of the length of time spent on pain responses are given for each immunogenic composition group for each post-treatment period of observation. Note, 0.1×GC rPorB=10 μg/ml GC rPorB and 1×GC rPorB=100 μg/ml GC rPorB. Table 4 summarizes the statistical analysis of the results given in Table 3. The p-values reported are the results from the rank-transform ANOVA approach. The statistical tests were confirmed by the Steel and Dwaas method. The * indicates that the Steel and Dwaas method yielded a non-significant statistic within 1 rank unit of the critical value (bordering significance).

As shown in Tables 3 and 4, a stronger pain response was detected for the Zw 3-14 alone and GC rPorB (100 μg/ml)+ Zw 3-14 immunogenic compositions than was detected in Example 1 (where only 0.1 ml injection volumes were used). The PBS negative control was well tolerated (Table 3) and elicited minimal pain behavior as expected (medians of 0 seconds, and 3 seconds for 0-10 and 10-20 minute time periods, respectively). Analysis of the pain responses during 0-10 minute time frame demonstrated that the samples which contained 0.05% Zw 3-14 were statistically different from the PBS buffer control (p≦0.0009 by rank-transformation ANOVA, compared to $\alpha$-level=0.01). See Table 4. In addition, during the 10-20 minute time frame, animals which received 0.2 ml of the clinical formulation of the GC rPorB immunogenic composition still exhibited significant pain responses as compared to PBS (p=0.0002, compared to $\alpha$-level=0.01). It was noteworthy that animals injected with immunogenic compositions containing 0.005% Zw 3-14 exhibited minimal pain responses, which were very similar to the responses induced by the PBS negative control. Because 0.05% Zw 3-14 is well above its CMC (0.004%-0.015%) these results suggested that the presence of Zw 3-14 above the CMC might be responsible for the pain on injection.

TABLE 3

Effect of Injection Volume on Pain Responses in Seconds.

| Immunogenic Composition | Vol. inject (ml) | N | 0-10 min Median | 0-10 min Mean (Range) | 10-20 min. Median | 10-20 min. Mean (Range) | 20-30 min. Median | 20-30 min. Mean (Range) |
|---|---|---|---|---|---|---|---|---|
| PBS | 0.1 | 4 | 1 | 2 (0-5) | 1 | 1 (0-4) | 1 | 1 (0-2) |
| PBS + 0.05% Zw 3-14 (1x) | 0.1 | 4 | 9 | 9 (2-14) | 2 | 6 (0-20) | 5 | 5 (0-9) |
| PBS + 0.005% Zw 3-14 (0.1x) | 0.1 | 4 | 0 | 0 (0-1) | 1 | 6 (0-24) | 0 | 0 (0-0) |
| 0.1x GC rPorB in PBS + 0.05% Zw 3-14 (1x) | 0.1 | 4 | 0 | 13 (0-52) | 0 | 4 (0-15) | 0 | 4 (0-14) |
| 1x GC rPorB in PBS + 0.05% Zw 3-14 (1x) | 0.1 | 4 | 3 | 10 (0-34) | 2 | 18 (0-66) | 3 | 9 (0-31) |
| 0.1x GC rPorB in PBS + 0.005% Zw 3-14 (0.1x) | 0.1 | 4 | 0 | 1 (0-2) | 2 | 3 (0-7) | 0 | 1 (0-2) |
| PBS | 0.2 | 6 | 0 | 2 (0-7) | 3 | 4 (0-15) | 1 | 8 (0-38) |
| PBS + 0.05% Zw 3-14 (1x) | 0.2 | 6 | 43 | 62 (3-197) | 52 | 46 (0-103) | 33 | 31 (0-51) |
| PBS + 0.005% Zw 3-14 (0.1x) | 0.2 | 4 | 5 | 13 (0-41) | 15 | 25 (0-70) | 5 | 5 (2-8) |
| 0.1x GC rPorB in PBS + 0.05% Zw 3-14 (1x) | 0.2 | 4 | 61 | 62 (18-107) | 19 | 23 (2-52) | 6 | 10 (1-27) |
| 1x GC rPorB in PBS + 0.05% Zw 3-14 (1x) | 0.2 | 6 | 66 | 88 (19-213) | 82 | 85 (30-156) | 4 | 12 (0-54) |
| 0.1x GC rPorB in PBS + 0.005% Zw 3-14 (0.1x) | 0.2 | 4 | 22 | 21 (0-38) | 19 | 28 (12-60) | 3 | 8 (0-27) |

TABLE 4

Statistical Analyses of Table 3 Data for Animals Injected With 0.2 ml of Immunogenic Composition (α-level = 0.05/5 = 0.01).

| Immunogenic Composition Compared with PBS alone | 0-10 min. | 10-20 min. |
|---|---|---|
| PBS + 0.05% Zw 3-14 (1x) | 0.0009* | 0.0143 |
| PBS + 0.005% Zw 3-14 (0.1x) | 0.2486 | 0.2672 |
| 10 µg/ml GC rPorB in PBS (0.1x) + 0.05% Zw 3-14 (1x) | 0.0003* | 0.1290 |
| 100 µg/ml GC rPorB in PBS (1x) + 0.05% Zw 3-14 (1x) | <0.0001 | 0.0002 |
| 10 µg/ml rPorB in PBS (0.1x) + 0.005% Zw 3-14 (0.1x) | 0.0761 | 0.0591 |

In view of the increased sensitivity obtained by injecting 200 µl of the above immunogenic compositions, the remaining examples will all employ a 200 µl injection volume for immunogenic composition and will keep formalin injections at 100 µl. The next study evaluates the immunogenic compositions comprising PFP-2+QS-21 as a positive control.

Example 3

Pain Responses on Injection of Immunogenic Compositions

Materials and Methods

Immunogenic composition preparation. Immunogenic compositions were prepared as described in Example 2. The PFP-2+QS-21 immunogenic composition, which is associated with pain upon injection in human volunteers, was used as a positive control.

Rat footpad pain testing. Rat footpad pain testing was performed as described in Example 1. In this Example, eight animals were in each group, and 0.2 ml injection volume was used.

Statistical analysis. Statistical analysis was performed as described in Example 1. In addition, a comparison of all three groups to each other was done using the rank-transform ANOVA approach with Tukey-Kramer adjustment for multiple comparisons.

Results

This study was performed to test whether the immunogenic composition PFP-2+QS-21 might serve as a positive control because it is associated with pain upon injection in human volunteers. These immunogenic compositions, except for formalin, were administered using the 0.2 ml injection volume. Table 5 summarizes the length of time spent on pain responses associated with injection of 0.2 ml of PFP-2+QS-21. The median, mean and range are given for each immunogenic composition group for each post-treatment period of observation. Note, one animal had a 52 second response which was excluded from data. Table 6 summarizes the statistical analysis of the results given in Table 5. The p-values reported are the results from the rank-transform ANOVA approach. The statistical tests were confirmed by the Steel and Dwaas method.

As shown in Table 5, both the PFP-2+QS-21 and GC rPorB immunogenic compositions gave painful responses during the first 10 minutes. These responses were significantly different ($p \leq 0.0002$, compared to α-level=0.05) from the responses induced by 0.2 ml PBS (negative control), which was again well tolerated (see Table 6).

The results of the first three Examples demonstrate that the two immunogenic composition preparations that were associated with pain on injection in human volunteers (GC rPorB+0.05% Zw 3-14; PFP-2+QS-21) also caused pain in the rat footpad (paw-lick) model when 0.2 ml of immunogenic composition was injected. The NTHi/Mcat immunogenic composition was not associated with pain upon injection into human volunteers, and did not cause pain in the rat footpad model (using 0.1 ml). The results further suggest that Zwittergent® 3-14 was a major source of the pain associated with the GC rPorB immunogenic composition. In contrast, reduction of the Zw 3-14 concentration to 0.005% (below the CMC), appeared to significantly reduce the pain responses. Based on these results, alternative formulations to remove or decrease Zw 3-14 were made and tested in this rat model.

TABLE 5

Pain Responses Injection of 0.2 ml of PFP-2 + QS-21.

| Immunogenic Composition | 0-10 min. time pain response sec | | | 10-20 min. time pain response sec | | |
|---|---|---|---|---|---|---|
| | N | Median | Mean (Range) | N | Median | Mean (Range) |
| PBS | 8 | 0 | 1 (0-6) | 7 | 0 | 0 (0-0)* |
| PFP-2 + QS-21 | 8 | 23 | 41 (5-117) | 8 | 0 | 10 (0-40) |
| GC rPorB in PBS + 0.05% Zw 3-14 | 8 | 53 | 56 (5-112) | 8 | 4 | 3 (0-11) |

TABLE 6

Statistical Analyses of Table 5 Data.
(P-values adjusted for multiple comparisons using the Tukey-Kramer method).

| Immunogenic Composition | 0-10 min. | 10-20 min. |
|---|---|---|
| GC rPorB in PBS + 0.05% Zw 3-14 vs. PBS | <0.0001 | 0.0747 |
| PFP-2 + QS-21 vs. PBS | 0.0002 | 0.1728 |
| GC rPorB in PBS + 0.05% Zw 3-14 vs. PFP2-QS-21 | 0.9494 | 0.8849 |

The next study was conducted at two different protein concentrations and evaluates the effect of diluting the detergent while keeping the protein component of a pain causing immunogenic composition constant on the induction of pain in the rat footpad model.

Example 4

Effect of Different Zwittergent® 3-14 OR GC rPorB Concentration on Pain Responses Materials and Methods Immunogenic composition preparation. Immunogenic compositions were prepared as described in Example 3.

Rat footpad pain testing. Rat footpad pain testing was performed as described in Example 1. In this Example, the pain responses were monitored for the first 20 minutes following injection, in part because of minimal pain responses observed in the 20-30 minutes period in the initial experiments. All immunogenic compositions (excluding the formalin positive control which is 0.1 ml) were tested using the 0.2 ml injection volume. The number of animals per group was increased to ten.

Statistical analysis. Statistical analysis was performed as described in Example 1.

Results

Table 7 summarizes the effect of different Zw 3-14 or GC rPorB concentrations on the length of time spent on pain responses using 0.2 ml injections. There were 10 animals in each group (Table 7). The median, mean and range are given for each immunogenic composition group for each post-treatment period of observation. Table 8 summarizes the statistical analysis of the results given in Table 7. The p-values reported are the results from the rank-transform ANOVA approach. The statistical tests were confirmed by the Steel and Dwaas method.

In one embodiment of the invention, the immunogenic composition is rendered more tolerable by diluting the pain causing detergent and keeping the protein component constant. Under these conditions, it is possible that the protein will be in a precipitated form and not soluble. Table 7 shows the results of a study that measured the responses induced by GC rPorB in 0.005% Zw 3-14, compared to the same protein dose in 0.05% Zw 3-14. At 0.005%, the Zw 3-14 is below the CMC, and the rPorin protein forms a fine precipitate. Previous studies had demonstrated that the protein was still immunogenic in this precipitated form (data not shown), and therefore this represented a formulation option that was considered as a possible way to overcome the pain. The results, presented in Table 7, show that the 100 µg/ml concentration of GC rPorB in 0.005% Zw 3-14 did not cause pain in the model, whereas the same concentration of GC rPorB in 0.05% Zw 3-14 again caused significant pain; the NTHi/Mcat clinical immunogenic composition again caused no pain. Statistical analysis demonstrated no significant difference between the responses induced by GC rPorB in 0.005% Zw 3-14 or NTHi/Mcat immunogenic composition when compared to the PBS group (Table 8). The pain responses induced by immunogenic compositions containing 0.05% Zw 3-14 were significantly higher during the 0-10 minute time frame as compared to PBS ($p<0.0001$, compared to $\alpha$-level=0.00625; Table 8).

TABLE 7

Effect of Different Zwittergent 3-14 or GC rPorB Concentrations on Pain Responses.

| Immunogenic Composition | 0-10 min. time pain response sec | | 10-20 min. time pain response sec | |
|---|---|---|---|---|
| | Median | Mean (Range) | Median | Mean (Range) |
| PBS | 0 | 1 (0-5) | 0 | 1 (0-6) |
| PBS + 0.05% Zw 3-14 (1x) | 18 | 18 (3-34) | 13 | 21 (0-84) |
| PBS + 0.005% Zw 3-14 (0.1x) | 0 | 0 (0-1) | 0 | 2 (0-9) |
| 10 µg/ml GC rPorB (0.1x) + 0.05% Zw 3-14 (1x) | 18 | 30 (0-143) | 23 | 28 (0-92) |
| 10 µg/ml GC rPorB (0.1x) + 0.005% Zw 3-14 (0.1x) | 11 | 10 (0-26) | 0 | 7 (0-47) |
| 100 µg/ml GC rPorB (1x) + 0.05% Zw 3-14 (1x) | 66 | 110 (0-279) | 49 | 79 (0-315) |
| 100 µg/ml GC rPorB (1x) + 0.005% Zw 3-14 (0.1x) | 1 | 13 (0-52) | 0 | 9 (0-25) |
| NTHi/Mcat. | 0 | 2 (0-13) | 9 | 14 (0-46) |
| 5% Formalin | 162 | 178 (20-331) | 173 | 174 (54-279) |

TABLE 8

Statistical Analyses of Table 7 Data (α-level = 0.05/8 = 0.00625).

| Immunogenic Composition Compared with PBS alone | 0-10 min. | 10-20 min. |
|---|---|---|
| PBS + 0.05% Zw 3-14 (1x) | <0.0001 | 0.0046 |
| PBS + 0.005% Zw 3-14 (0.1x) | 0.6935 | 0.3616 |
| 10 µg/ml GC rPorB (0.1x) + 0.05% Zw 3-14 (1x) | <0.0001 | 0.0037 |
| 10 µg/ml GC rPorB + 0.005% Zw 3-14 (0.1x) | 0.0126 | 0.4730 |
| 100 µg/ml GC rPorB (1x) + 0.05% Zw 3-14 (1x) | <0.0001 | <0.0001 |
| 100 µg/ml GC PorB (1x) + 0.005% Zw 3-14 (0.1x) | 0.0419 | 0.1450 |
| NTHi/Mcat. | 0.8410 | 0.0181 |
| 5% Formalin | <0.0001 | <0.0001 |

This example showed how the tolerability of an immunogenic composition can be improved by diluting the pain causing detergent and keeping the protein component constant. The next example shows how to make an immunogenic composition having improved tolerability by first identifying a non-pain causing detergent and then exchanging the pain causing detergent for a non pain causing detergent. This approach also shows how the solubility of the protein component can be maintained.

Example 5

Effect of Triton® X-100 on Pain Responses Induced by GC rPorB

Materials and Methods

Immunogenic composition preparation. Immunogenic compositions were prepared as described in Example 3.

Detergent Exchange. The replacement or exchange of the detergent associated with the GC rPorB (e.g. replacing Zw 3-14 with TX) was accomplished by ion exchange chromatography. Briefly, the GC rPorB, in 10 mM NaPO$_4$ (pH 7.4), 150 mM NaCl, 0.05% (w/v) Zw 3-14 was loaded onto a column of Q-Sepharose™ (Amersham-Pharmacia Biotech, Piscataway, N.J.), which was equilibrated in the same buffer. The bound protein was washed with approximately 900 ml of 20 mM Tris (pH 8), 0.03% (v/v) TX containing 25 nM NaCl. The protein was eluted using a linear gradient of NaCl in 20 mM Tris (pH 8), 0.03% (v/v) TX. Fractions containing the GC PorB were pooled and the TX concentration was adjusted to 0.06% (v/v) by adding TX directly. The pooled material was then dialyzed against 10 mM NaPO$_4$ (pH 7.4), 150 mM NaCl containing 0.06% (v/v) TX. The dialyzed material was passed through a 0.22 µm membrane filter and the protein concentration of the filtered material was determined.

Rat footpad pain testing. Rat footpad pain testing was performed as described in Example 4. In the present Example there were eight animals per group.

Statistical Analysis. Statistical Analysis was performed as described in Example 1.

Results

Because the NTHi/Mcat immunogenic composition contains Zwittergent® 3-12 below the CMC and also contains TX at 0.04% (v/v) which is above the CMC for TX, it was of interest to consider TX as an alternative detergent for GC rPorB, in particular because the mixture of TX and Zw 3-12 was not associated with pain-on-injection in human volunteers.

Table 9 summarizes the effect of TX on the length of time spent on pain responses induced by GC rPorB using 0.2 ml injection volumes. There were 8 animals in each group. The median, mean and range are given for each immunogenic composition group for each post-treatment period of observation. Note, Al gel=250 µg/ml aluminum as AlPO$_4$. Table 10 summarizes the statistical analysis of the results given in Table 9. The p-values reported are the results from the rank-transform ANOVA approach. The statistical tests were confirmed by the Steel and Dwaas method. The * indicates that the Steel and Dwaas method yielded a non-significant statistic within 1 rank unit of the critical value (bordering significance).

Animals injected with GC rPorB (100 µg/ml) in 0.06% TX showed virtually no pain responses at both the 0-10 minute and the 10-20 minute time frames (p=0.98 and 0.55, respectively, compared to α-level=0.01). These responses were similar to the responses induced by PBS alone (Tables 9 and 10). These data demonstrate that exchanging Zw 3-14 with TX resulted in significant reduction in pain responses.

TABLE 9

Effect of Triton X-100 on Pain Responses Induced by GC rPorB

| | 0-10 min. time pain response sec | | 10-20 min. time pain response sec | |
|---|---|---|---|---|
| Immunogenic Composition | Median | Mean (Range) | Median | Mean (Range) |
| PBS | 0 | 5 (0-37) | 0 | 6 (0-45) |
| PBS + 0.06% TX | 2 | 8 (0-34) | 0 | 2 (0-15) |
| GC rPorB in PBS + 0.05% Zw 3-14 | 168 | 164 (26-300) | 197 | 232 (0-600) |
| GC RPORB IN PBS + 0.06% TX (EXCHANGED FROM ZW 3-14) | 0 | 8 (0-58) | 0 | 2 (0-13) |
| NTHI/MCAT | 0 | 2 (0-11) | 0 | 0 (0-1) |
| NTHi/Mcat + Al gel | 11 | 36 (0-191) | 25 | 45 (0-131) |

TABLE 10

Statistical Analyses for Table 9 (α-level = 0.05/5 = 0.01).

| Immunogenic Composition Compared with PBS alone | 0-10 min. | 10-20 min. |
|---|---|---|
| PBS + 0.05% TX | 0.2061 | 0.5677 |
| GC rPorB in PBS + 0.05% Zw 3-14 | <0.0001 | 0.0002* |
| GC rPorB in PBS + 0.06% TX (no Zw 3-14) | 0.9794 | 0.5495 |
| NTHi/Mcat | 0.7376 | 0.4967 |
| NTHi/Mcat + Al gel | 0.0190 | 0.0318 |

From a practical standpoint exchanging detergents requires at least one additional step where protein can be lost or expense can otherwise be incurred. Therefore, the next example teaches how to design a solution to the pain problem where the pain causing detergent is diluted to a non painful level with a non-pain inducing detergent.

Example 6

Effect of Diluting GC rPorB/ZW 3-14 into Triton® X-100 Buffer

Materials and Methods

Immunogenic composition preparation by dilution. As an alternative to detergent exchange, the possibility of using existing batch concentrate material, which was in PBS containing 0.05% Zw 3-14 and diluting this material directly into a buffer containing 0.05% TX was examined. This dilution results in an immunogenic composition having improved tolerability, which contains residual amounts of Zw 3-14 (~0.004%), but at a concentration below the CMC.

Rat footpad pain testing. Rat footpad pain testing was performed as described in Example 4. There were 10 animals per group.

Statistical analysis. Statistical Analysis was performed as described in Example 1.

Results

Table 11 summarizes the effect of diluting GC rPorB/Zw 3-14 into TX buffer using 0.2 ml injection volumes. There were 10 animals per group. The median, mean and range of the length of time spent on pain response are given for each immunogenic composition group for each post-treatment period of observation. Table 12 summarizes the statistical analysis of the results given in Table 11. The p-values reported are the results from the rank-transform ANOVA approach. The statistical tests were confirmed by the Steel and Dwaas method. The ** indicates a clear disagreement between the ANOVA and Steel and Dwaas methods.

The immunogenic composition diluted directly into buffer containing 0.05% TX also yielded a preparation that did not cause pain in the footpad model. This was similar to the pain responses to PBS alone, PBS combined with TX and PBS and Zw 3-14 diluted into TX (see Tables 11 and 12). In this example, the protein solubility is maintained in the TRITON.

TABLE 11

Effect of diluting GC rPorB/Zw 3-14 into Triton X-100 Buffer.

| Immunogenic Composition | 0-10 min. time pain response sec | | 10-20 min. time pain response sec | |
| --- | --- | --- | --- | --- |
| | Median | Mean (Range) | Median | Mean (Range) |
| PBS | 0 | 1 (0-5) | 0 | 0 (0-2) |
| PBS + 0.05% TX | 0 | 3 (0-16) | 0 | 0 (0-0) |
| PBS + 0.05% Zw 3-14 diluted into PBS + 0.05% TX | 0 | 2 (0-13) | 0 | 3 (0-21) |
| GC rPorB in 0.05% Zw 3-14 | 64 | 102 (0-263) | 45 | 47 (0-126) |
| GC rPorB in 0.05% Zw 3-14 diluted into PBS + 0.05% TX | 0 | 0 (0-0) | 0 | 1 (0-10) |
| GC rPorB in 0.06% TX (exchanged from Zw 3-14) | 1 | 9 (0-48) | 0 | 0 (0-0) |
| 5% Formalin | 219 | 225 (51-366) | 181 | 167 (4-310) |

TABLE 12

Statistical Analyses for Table 11 ($\alpha$-level = 0.05/6 = 0.00833).

| Immunogenic Composition Compared with PBS alone | 0-10 min. | 10-20 min. |
| --- | --- | --- |
| PBS + 0.05% TX | 0.1420 | 0.5550 |
| PBS + 0.05% Zw 3-14 diluted into PBS + 0.05% TX | 0.3445 | 0.4662 |
| GC rPorB in 0.05% Zw 3-14 | <0.0001 | <0.0001** |
| GC rPorB in 0.05% Zw 3-14 diluted into PBS + 0.05% TX | 0.6287 | 0.9446 |
| GC rPorB in 0.06% TX(exchanged from Zw 3-14) | 0.0296 | 0.5550 |
| 5% Formalin | <0.0001 | <0.0001 |

Next, we evaluated whether other buffer systems and other non-ionic detergents could also be useful in producing immunogenic compositions having improved tolerability.

Example 7

Pain Responses to GC rPorB Formulated in Tris Buffered Saline Containing Triton® X-100 or Reduced Triton® X-100

Materials and Methods

Immunogenic composition preparation. Immunogenic compositions were prepared as described in Example 6. Existing batch concentrations of GC rPorB were diluted in reduced TX.

Rat footpad pain testing. Rat footpad pain testing was performed as described in Example 4. There were 10 animals per group. TBS was used in place of PBS.

Statistical analysis. Statistical Analysis was performed as described in Example 1.

Results

Table 13 summarizes the length of time spent on pain responses to 0.2 ml injections of GC rPorB formulated in TBS containing TX or reduced TX. Reduced TX is an analog of TX-100 that absorbs less at 280 nm, thus making it easier to work with and more acceptable. The median, mean and range are given for each immunogenic composition group for each post-treatment period of observation. There were 10 animals per group. Table 14 summarizes the statistical analysis of the results given in Table 13. The p-values reported are the results from the rank-transform ANOVA approach. The statistical tests were confirmed by the Steel and Dwaas method. Note, TBS=10 mM Tris (pH 7.5), 150 mM NaCl.

A similar result was obtained when 0.05% of either TX or reduced TX was used in a TBS diluent, a change done to permit GC rPorB to bind to the adjuvant aluminum hydroxide (See Table 13). The results for either the TX or reduced TX compositions were statistically indistinguishable from the buffer control (see Table 14).

TABLE 13

Pain Responses to 0.2 ml injections of GC rPorB Formulated in Tris Buffered Saline Containing Triton X-100 or Reduced Triton X-100.

| Immunogenic Composition | 0-10 min time pain response sec | | 10-20 min. time pain response sec | |
|---|---|---|---|---|
| | Median | Mean (Range) | Median | Mean (Range) |
| TBS | 0 | 4 (0-25) | 0 | 4 (0-17) |
| GC rPorB in PBS + 0.05% Zw 3-14 | 53 | 83 (0-206) | 20 | 30 (0-126) |
| GC rPorB in PBS + 0.05% Zw 3-14 diluted into PBS + 0.05% TX | 0 | 10 (0-35) | 6 | 16 (0-85) |
| GC rPorB in PBS + 0.05% Zw 3-14 diluted into PBS + 0.05% red. TX | 0 | 8 (0-61) | 0 | 6 (0-34) |
| PBS + 0.05% Zw 3-14 diluted into TBS + 0.05% TX | 12 | 17 (0-50) | 1 | 6 (0-44) |
| PBS + 0.05% Zw 3-14 diluted into TBS + 0.05% red. TX | 0 | 4 (0-32) | 1 | 3 (0-12) |
| 5% Formalin | 233 | 252 (97-457) | 448 | 435 (303-523) |

TABLE 14

Statistical Analyses for Table 13 ($\alpha$-level = 0.05/6 = 0.00833).

| Immunogenic Composition Compared with TBS alone | 0-10 min. | 10-20 min. |
|---|---|---|
| GC rPorB in PBS + 0.05% Zw 3-14 | <0.0001 | 0.0417 |
| GC rPorB in PBS + 0.05% Zw 3-14 diluted into PBS + 0.05% TX | 0.4736 | 0.1865 |
| GC rPorB in PBS + 0.05% Zw 3-14 diluted into PBS + 0.05% reduced TX | 0.8280 | 0.9401 |
| PBS + 0.05% Zw 3-14 diluted into TBS + 0.05% TX | 0.0395 | 0.8383 |
| PBS + 0.05% Zw 3-14 diluted into TBS + 0.05% red. TX | 0.8968 | 0.9037 |
| 5% Formalin | <0.0001 | <0.0001 |

Diluting micelles of a pain inducing detergent to a level below it's critical micelle concentration and adding a non-pain inducing detergent to a level above its CMC produced a highly tolerable immunogenic composition. In the next example, it was evaluated whether a solution to the pain problem could be designed where the pain causing detergent is maintained above its CMC, but a non-pain inducing detergent is added to create mixed micelles and alleviate the pain.

Example 8

Converting a Painful Immunogenic Composition into a Non-Painful One by Adding Triton® X-100 and Keeping Zwittergent® 3-12 Constant

Materials and Methods

Injection preparation. Preparations of the following detergents and detergent combinations were evaluated in the rat footpad model: 0.2% Zw 3-12 in PBS; 0.2% Zw 3-12 with 0.002% TX; 0.2% Zw 3-12 with 0.01% TX; 0.2% Zw 3-12 diluted into 0.05% TX; 0.2% Zw 3-12 diluted into 0.2% TX.

Rat footpad pain testing. Rat footpad pain testing was performed as described in Example 4. There were 10 animals per group.

Statistical analysis. Statistical Analysis was performed as described in Example 1. (data not shown).

Results

FIG. 1 shows the resulting pain induced by injecting Zw 3-12 compared to Zw 3-12 with different concentrations of TX added. For example, 0.2% Zw 3-12 undiluted and 0.2% Zw 3-12 with 0.002% TX cause a relatively large amount of pain as demonstrated by the rat footpad model. In these formulations, the concentration of the pain inducing zwitterionic detergent was held constant at 0.2% Zw 3-12 and increasing amounts of a second non-painful nonionic detergent (TX) was added to create mixed micelles. As shown in FIG. 1, adding 0.01% TX, 0.05% TX or 0.2% TX to solutions of 0.2% Zw 3-12 results in a dramatic reduction in pain response when injected into the rats in the rat footpad model.

As can be seen from the plot, addition of Triton X-100 to a solution of 0.2% Zwittergent 3-12 (final concentration), resulted in a reduction in the pain response. This effect seems to become pronounced when a concentration of 0.01% Triton X-100 is reached and the pain mediation continues Triton X-100 is added up to 0.2% final concentration. These results, go against what one would anticipate. Normally it would be predicted that the more detergent one adds to an immunogenic composition, the better that solution is able to solubilize cells and the more pain should be induced.

Statistical analysis of the data reveals that at time 0-10 min: the only non significant test is for the groups with lowest Triton X-100 compared with the negative control (e.g. 0.05% Triton X-100 alone). Similarly, at time 10-20 min: that same comparison is non significant and furthermore the 0.01% Triton X-100 mixture is not significantly different from the negative control.

It may be concluded that by adding 0.01% Triton X-100 to a solution of 0.2% Zwittergent 3-12, one has generated mixed micelles of both Zwittergent 3-12 and Triton X-100 and that these micelles have physical properties in solution which result in less pain upon injection of this solution.

In the next example, various detergents were evaluated for tolerability by measuring pain induction in the rat foot pad model.

Example 9

Tolerability of Various Detergents

Materials and Methods

Injection preparation. The detergents listed in Tables 15, 16 and 17 were prepared at the indicated concentrations which was above the CMC for each detergent. All injections were of a volume of 200 µl except for formalin which was 100 µl.

Rat footpad pain testing. Rat footpad pain testing was performed as described in Example 4. There were 8 animals per group.

Results

A survey of detergents was performed to determine which zwitterionic, non-ionic and ionic detergents were pain causing and which were not pain causing when injected at concentrations above the CMC for the detergent. The results reveal that the nonionic detergents TRITON X-100, reduced TRITON X-100, TWEEN 80 and BRIJ are highly tolerable when injected and do not cause significant pain in the rat foot pad model. See Tables 15, 16 and 17. In contrast, the zwitterionic detergents ZWITTERGENT 3-10, ZWITTERGENT 3-12, ZWITTERGENT 3-14, CHAPS, and EMPIGEN BB all caused significant pain in the rat footpad model and would probably not be suitable for use in immunogenic compositions. Likewise, the nonionic detergents dodecyl maltoside and octyl glucoside induced pain in the rat footpad model.

TABLE 15

Survey of Pain Induced by Various Detergents in Rat Footpad Model

| Detergent* | Concentration | Mean time pain response (sec.) | | Standard deviation | |
|---|---|---|---|---|---|
| | | 0-10 min. | 10-20 min. | 0-10 min. | 10-20 min. |
| TX (NI) | 0.05% | 8.5 | 11.2 | 14.7 | 23 |
| red TX(NI) | 0.05% | 0.1 | 4.3 | 0.3 | 7.4 |
| Zw3-14 (ZW) | 0.05% | 44.7 | 33.6 | 34.6 | 31 |
| Zw3-14 (ZW) | 0.05% | 37.8 | 30.1 | 55.4 | 51.7 |
| Zw3-12 (ZW) | 0.05% | 295.3 | 139.8 | 103.4 | 115.1 |
| PBS | N/A | 6.2 | 11.9 | 15.1 | 18 |
| Formalin | 5% | 161.3 | 313.5 | 125 | 138 |

*NI—nonionic; ZW—zwitterionic,

TABLE 16

Survey of Pain Induced by Various Detergents in Rat Footpad Model

| Detergent* | Concentration | Mean time pain response (sec.) | | Standard deviation | |
|---|---|---|---|---|---|
| | | 0-10 min. | 10-20 min. | 0-10 min. | 10-20 min. |
| Octyl glucoside (NI) | 1% | 48 | 108 | 54 | 72 |
| CHAPS (ZW) | 0.9% | 351 | 114 | 158 | 129 |
| PBS | | 3 | 0.4 | 8 | 1 |
| Tween80 (NI) | 0.025% | 3 | 6 | 7 | 11 |
| BRIJ35 (NI) | 0.02% | 1 | 0 | 3 | 1 |
| Formalin | 5% | 114 | 218 | 93 | 110 |

*NI—nonionic; ZW—zwitterionic,

TABLE 17

Survey of Pain Induced by Various Detergents in Rat Footpad Model

| Detergent* | Concentration | Mean time pain response (sec.) | | Standard deviation | |
|---|---|---|---|---|---|
| | | 0-10 min. | 10-20 min. | 0-10 min. | 10-20 min. |
| Mega10 (NI) | 7 mM | 28.8 | 31.0 | 35.1 | 28.6 |
| Dodecyl maltoside (NI) | 0.8% | 298.0 | 141.0 | 148.2 | 106.7 |
| Emipgen BB (ZW) | 0.09% | 44.3 | 6.1 | 117.7 | 12.4 |
| TBS | N/A | 0.0 | 0.0 | 22.8 | 0.0 |
| Sodium (I) deoxycholate | 0.5% | 307.0 | 121.9 | 170.0 | 112.6 |
| Zwitt 3-10 (ZW) | 0.8% | 300.6 | 260.5 | 125.0 | 160.7 |
| Formalin | 5% | 272.5 | 280.4 | 81.2 | 58.5 |

*NI—nonionic; ZW—zwitterionic, I—ionic

In the next example we sought to verify that other hydrophobic proteins showed the same pattern of tolerability as did gonococcal PorB.

Example 10

Pain Responses on Injection of Immunogenic Compositions with Recombinant Meningococcal PorA (Class I Porin)

Materials and Methods

Immunogenic composition preparation. Immunogenic compositions were prepared as described in Example 2.

Rat footpad pain testing. Rat footpad pain testing was performed as described in Example 1. In this Example, ten animals were in each group, and 0.2 ml injection volumes were used.

Results

This study was performed to test whether the recombinant porin protein meningococcal PorA (Class I porin) would show the same pattern of tolerability as did the gonococcal PorB in the previous examples.

The results indicate that meningococcal PorA displays the same pattern of tolerability as gonococcal PorB when combined in immunogenic compositions with ZWITTERGENT 3-14 and TRITON X-100 and evaluated in the rat footpad model. See Table 18. Immunogenic compositions comprising meningococcal PorA and ZWITTERGENT 3-14 induced pain in the rat footpad model while immunogenic compositions comprising meningococcal PorA and TRITON X-100 were much more tolerable in that they induced far less pain in the rat footpad model than did meningococcal PorA and ZWITTERGENT 3-14.

The data in Table 18 also show that addition of the adjuvant AlOH had no effect either positive or negative of the level of pain induced and therefore on the tolerability of the immunogenic composition. See Table 18.

TABLE 18

Pain Induced by Immunogenic Compositions With Meningococcal Porin Por A as the Hydrophobic Protein

| Detergent | Mean time pain response (sec.) | | Standard deviation | |
|---|---|---|---|---|
| | 0-10 min. | 10-20 min. | 0-10 min. | 10-20 min. |
| GC porB/Zw | 26 | 37 | 22 | 46 |
| NTHi/M.cat | 2 | 10 | 7 | 28 |
| Mn PorA/Zw + AlOH | 35 | 50 | 25 | 122 |
| Mn PorA/TX + AlOH | 7 | 3 | 15 | 6 |
| Tris/Zw + AlOH | 26 | 6 | 22 | 13 |
| Tris/TX + AlOH | 4 | 6 | 8 | 16 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entirety for all purposes.

What is claimed is:

1. A non-painful immunogenic composition of a hydrophobic protein suitable for injection in a human comprising:
   (a) a hydrophobic protein;
   (b) an amount of a zwitterionic detergent that is less than the amount required to solubilize the protein; and
   (c) an amount of a pharmaceutically acceptable nonionic detergent effective to maintain solubility of the protein in a pharmaceutically acceptable carrier and,
   wherein the zwitterionic detergent is selected from the group consisting of n-Octyl-N,N-dimethyl-3-ammonio-1-propanesulfonate; n-Decyl-N,N-dimethyl-3-ammonio-1-propanesulfonate; n-Dodecyl-N,N-dimethyl-3-ammonio-1-propanesulfonate; n-Tetradecyl-N,N-dimethyl-3-ammonio-1-propanesulfonate; 3-(N,N-n-Hexadecyl-N,N-dimethyl-3-ammonio-1-propanesulfonate; 3-[(3-Cholamidopropyl)dimethylammonio]-1-propanesulfonate; 3-[(3-Cholamidopropyl)dimethylammonio]-2-hydroxy-1-propanesulfonate; and n-Dodecyl-N,N-dimethylglycine.

2. The composition of claim 1, wherein the zwitterionic detergent is n-Tetradecyl-N,N-dimethyl-3-ammonio-1-propanesulfonate.

3. The composition of claim 1, wherein the nonionic detergent is selected from the group consisting of alpha-[4-(1,1,3,3-tetramethylbutyl)phenyl]-omega-hydroxypoly(oxy-1,2-ethanediyl), Polyoxyethylene (20) sorbitan monolaurate, Polyoxyethylene (20) sorbitan monooleate and Polyoxyethylene (35) Lauryl Ether.

4. The composition of claim 3, wherein the nonionic detergent is alpha-[4-(1,1,3,3-tetramethylbutyl)phenyl]-omega-hydroxypoly(oxy-1,2-ethanediyl).

5. The composition of claim 1, wherein the zwitterionic detergent is n-Tetradecyl-N,N-dimethyl-3-ammonio-1-propanesulfonate in a final concentration that is below its critical micelle concentration (CMC) and the nonionic detergent is alpha-[4-(1,1,3,3-tetramethylbutyl)phenyl]-omega-hydroxypoly(oxy-1,2-ethanediyl) in a final concentration that is above its CMC.

6. The composition of claim 1, wherein the hydrophobic protein is a porin.

7. The composition of claim 6, wherein the porin is selected from the group consisting of a gonococcal porin or a Meningococcal porin.

8. A method for producing a less-painful immunogenic composition of a hydrophobic protein in a pharmaceutically acceptable carrier suitable for administering to a mammal, comprising the steps of
   (a) solubilizing said hydrophobic protein with a zwitterionic detergent to make a first composition;
   (b) altering said first composition, such that the altered composition is less painful as compared to said first composition,
   wherein the altering step (b) is selected from the group consisting of (i) diluting the zwitterionic detergent where the hydrophobic protein is in a precipitated form, (ii) exchanging the zwitterionic detergent with a non-pain causing nonionic detergent, and (iii) adding a non-pain causing nonionic detergent but keeping the concentration of the zwitterionic detergent constant.

9. The method of claim 8, wherein the zwitterionic detergent is selected from the group consisting of n-Octyl-N,N-dimethyl-3-ammonio-1-propanesulfonate; n-Decyl-N,N-dimethyl-3-ammonio-1-propanesulfonate; n-Dodecyl-N,N-dimethyl-3-ammonio-1-propanesulfonate; n-Tetradecyl-N,N-dimethyl-3-ammonio-1-propanesulfonate; 3-(N,N-n-Hexadecyl-N,N-dimethyl-3-ammonio-1-propanesulfonate; 3-[(3-Cholamidopropyl)dimethylammonio]-1-propanesulfonate; 3-[(3-Cholamidopropyl)dimethylammonio]-2-hydroxy-1-propanesulfonate; and n-Dodecyl-N,N-dimethylglycine.

10. The method of claim 9, wherein the zwitterionic detergent is n-Tetradecyl-N,N-dimethyl-3-ammonio-1-propanesulfonate.

11. The method of claim 8, wherein the nonionic detergent is selected from the group consisting of alpha-[4-(1,1,3,3-tetramethylbutyl)phenyl]-omega-hydroxypoly(oxy-1,2-ethanediyl), Polyoxyethylene (20) sorbitan monolaurate, Polyoxyethylene (20) sorbitan monooleate and Polyoxyethylene (35) Lauryl Ether.

12. The method of claim 11, wherein the nonionic detergent is alpha-[4-(1,1,3,3-tetramethylbutyl)phenyl]-omega-hydroxypoly(oxy-1,2-ethanediyl).

13. The method of claim 8, wherein the zwitterionic detergent is n-Tetradecyl-N,N-dimethyl-3-ammonio-1-propanesulfonate in a final concentration that is below its CMC and the nonionic detergent is alpha-[4-(1,1,3,3-tetramethylbutyl)phenyl]-omega-hydroxypoly(oxy-1,2-ethanediyl) in a final concentration that is above its CMC.

14. The method of claim 8, wherein the hydrophobic protein is a porin.

15. The method of claim 14, wherein the porin is selected from the group consisting of a gonococcal porin or a Meningococcal porin.

16. The method of claim 8, wherein the zwitterionic detergent is diluted to below the critical micelle concentration.

17. A method of reducing the pain associated with administering an immunogenic composition comprising a hydrophobic protein and a zwitterionic detergent into a mammal, which method comprises
   (a) altering said composition, such that the altered composition is less painful as compared to the unaltered composition, and
   (b) administering said immunogenic composition,
   wherein the altering step (a) is selected from the group consisting of (i) diluting said zwitterionic detergent where the hydrophobic protein is in a precipitated form, (ii) exchanging said zwitterionic detergent with a non-pain causing nonionic detergent, and (iii) adding a non-pain causing nonionic detergent but keeping the concentration of the zwitterionic detergent constant.

18. The method of claim 17, wherein said zwitterionic detergent is selected from the group consisting of n-Octyl-N,N-dimethyl-3-ammonio-1-propanesulfonate; n-Decyl-N,N-dimethyl-3-ammonio-1-propanesulfonate; n-Dodecyl-N,N-dimethyl-3-ammonio-1-propanesulfonate; n-Tetradecyl-N,N-dimethyl-3-ammonio-1-propanesulfonate; 3-(N,N-n-Hexadecyl-N,N-dimethyl-3-ammonio-1-propanesulfonate; 3-[(3-Cholamidopropyl)dimethylammonio]-1-propanesulfonate; 3-[(3-Cholamidopropyl)dimethylammonio]-2-hydroxy-1-propanesulfonate; and n-Dodecyl-N,N-dimethylglycine.

19. The method of claim 18, wherein the nonionic detergent is selected from the group consisting of alpha-[4-(1,1,3,3-tetramethylbutyl)phenyl]-omega-hydroxypoly(oxy-1,2-ethanediyl), Polyoxyethylene (20) sorbitan monolaurate, Polyoxyethylene (20) sorbitan monooleate and Polyoxyethylene (35) Lauryl Ether.

20. The method of claim 19, wherein the nonionic detergent is alpha-[4-(1,1,3,3-tetramethylbutyl)phenyl]-omega-hydroxypoly(oxy-1,2-ethanediyl).

21. The method of claim 18, wherein the zwitterionic detergent is n-Tetradecyl-N,N-dimethyl-3-ammonio-1-propanesulfonate in a final concentration that is below its CMC and the nonionic detergent is alpha-[4-(1,1,3,3-tetramethylbutyl)phenyl]-omega-hydroxypoly(oxy-1,2-ethanediyl) in a final concentration that is above its CMC.

22. The method of claim 17, wherein the hydrophobic protein is an integral membrane protein.

23. The method of claim 22, wherein the integral membrane protein is selected from the group consisting of a gonococcal porin or a meningococcal porin.

24. The method of claim 17, wherein the solubility of the hydrophobic protein is maintained in said nonionic detergent.

25. A method of reducing the pain associated with administering an immunogenic composition comprising a hydrophobic protein and a zwitterionic detergent into a mammal, which method comprises
(a) altering said composition, such that the altered composition produces a reduction in pain as measured in the rat footpad model as compared to the unaltered composition, and
(b) administering said immunogenic composition
wherein the altered composition produces at least about a 50% reduction in pain as measured in the rat footpad model as compared to the unaltered composition.

26. The method of claim 25, wherein the altering step (a) is selected from the group consisting of (i) diluting said zwitterionic detergent with a non-pain causing nonionic detergent wherein the hydrophobic protein is in a precipitated form, (ii) exchanging the zwitterionic detergent with a non-pain causing nonionic detergent, and (iii) adding a non-pain causing nonionic detergent but keeping the concentration of the zwitterionic detergent constant.

27. The method of claim 26, wherein the altering step (a) is diluting the zwitterionic detergent with a non-pain causing nonionic detergent wherein the hydrophobic protein is in a precipitated form.

28. The method of claim 26, wherein the altering step (a) is exchanging the zwitterionic detergent with a non-pain causing nonionic detergent.

29. The method of claim 26, wherein the altering step (a) is adding a non-pain causing nonionic detergent but keeping the concentration of the zwitterionic detergent constant.

30. The method of any of claims 27, 28 and 29, wherein the zwitterionic detergent is selected from the group consisting of n-Octyl-N,N-dimethyl-3-ammonio-1-propanesulfonate; n-Decyl-N,N-dimethyl-3-ammonio-1-propanesulfonate; n-Dodecyl-N,N-dimethyl-3-ammonio-1-propanesulfonate; n-Tetradecyl-N,N-dimethyl-3-ammonio-1-propanesulfonate; 3-(N,N-n-Hexadecyl-N,N-dimethyl-3-ammonio-1-propanesulfonate; 3-[(3-Cholamidopropyl)dimethylammonio]-1-propanesulfonate; 3-[(3-Cholamidopropyl)dimethylammonio]-2-hydroxy-1-propanesulfonate; and n-Dodecyl-N,N-dimethylglycine.

31. The method of any of claims 27, 28 and 29, wherein the zwitterionic detergent is n-Tetradecyl-N,N-dimethyl-3-ammonio-1-propanesulfonate.

32. The method of any of claims 27, 28 and 29, wherein the nonionic detergent is selected from the group consisting of alpha-[4-(1,1,3,3-tetramethylbutyl)phenyl]-omega-hydroxypoly(oxy-1,2-ethanediyl), Polyoxyethylene (20) sorbitan monolaurate, Polyoxyethylene (20) sorbitan monooleate and Polyoxyethylene (35) Lauryl Ether.

33. The method of any of claims 27, 28 and 29, wherein the nonionic detergent is alpha-[4-(1,1,3,3-tetramethylbutyl)phenyl]-omega-hydroxypoly(oxy-1,2-ethanediyl).

34. The method of any of claims 27, 28 and 29, wherein the zwitterionic detergent is n-Tetradecyl-N,N-dimethyl-3-ammonio-1-propanesulfonate in a final concentration that is below its CMC and the nonionic detergent is alpha-[4-(1,1,3,3-tetramethylbutyl)phenyl]-omega-hydroxypoly(oxy-1,2-ethanediyl) in a final concentration that is above its CMC.

35. A method of maintaining solubility of a hydrophobic protein in an immunogenic composition, which method comprises:
solubilizing a hydrophobic protein in a non-pain causing nonionic detergent, wherein non-pain causing nonionic detergent is alpha-[4-(1,1,3,3-tetramethylbutyl)phenyl]-omega-hydroxypoly(oxy-1,2-ethanediyl).

36. A method for immunizing humans with compositions containing hydrophobic membrane proteins without causing pain, which method comprises selecting alpha-[4-(1,1,3,3-tetramethylbutyl)phenyl]-omega-hydroxypoly(oxy-1,2-ethanediyl (Triton X-100) as a pharmaceutically acceptable detergent for maintaining solubility of hydrophobic proteins in the final formulation; wherein the concentration of Triton X-100 is above the CMC.

37. The immunogenic composition of claim 1 further comprising a pharmaceutically acceptable carrier.

38. The immunogenic composition of claim 1 further comprising an adjuvant.

* * * * *